(12) United States Patent
Oliver-Shaffer et al.

(10) Patent No.: US 9,108,961 B2
(45) Date of Patent: Aug. 18, 2015

(54) CRYSTALLINE FORM OF (R)-7-CHLORO-N-(QUINUCLIDIN-3-YL)BENZO[B]THIOPHENE-2-CARBOXAMIDE HYDROCHLORIDE

(71) Applicant: EnVivo Pharmaceuticals, Inc., Watertown, MA (US)

(72) Inventors: Patricia Oliver-Shaffer, Acton, MA (US); Gideon Shapiro, Gainesville, FL (US); Richard Chesworth, Concord, MA (US); Muneki Kishida, Osaka (JP); Takayuki Ishige, Osaka (JP)

(73) Assignee: Forum Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 14/184,453

(22) Filed: Feb. 19, 2014

(65) Prior Publication Data

US 2014/0249179 A1 Sep. 4, 2014

Related U.S. Application Data

(63) Continuation of application No. 13/698,759, filed as application No. PCT/US2011/036844 on Feb. 17, 2011, now Pat. No. 8,710,227.

(60) Provisional application No. 61/345,363, filed on May 17, 2010, provisional application No. 61/352,092, filed on Jun. 7, 2010.

(51) Int. Cl.
*A61K 31/44* (2006.01)
*C07D 453/02* (2006.01)

(52) U.S. Cl.
CPC .................................. *C07D 453/02* (2013.01)

(58) Field of Classification Search
None
See application file for complete search history.

(56) References Cited

U.S. PATENT DOCUMENTS

| | | | |
|---|---|---|---|
| 4,605,652 A | 8/1986 | Welstead, Jr. | |
| 4,721,720 A | 1/1988 | Wootton et al. | |
| 4,783,478 A | 11/1988 | Wootton et al. | |
| 4,851,407 A | 7/1989 | Wootton et al. | |
| 4,985,420 A | 1/1991 | Hamminga et al. | |
| 5,069,904 A | 12/1991 | Masterson | |
| 5,114,947 A | 5/1992 | Imondi | |
| 5,122,528 A | 6/1992 | Imondi | |
| 5,198,437 A | 3/1993 | Hamminga et al. | |
| 5,561,149 A | 10/1996 | Azria et al. | |
| 5,599,937 A | 2/1997 | Glas et al. | |
| 5,656,638 A | 8/1997 | Gaeta et al. | |
| 5,703,116 A | 12/1997 | Gaeta et al. | |
| 5,760,062 A | 6/1998 | Gaeta et al. | |
| 5,863,936 A | 1/1999 | Gaeta et al. | |
| 5,902,814 A | 5/1999 | Gordon et al. | |
| 5,977,144 A | 11/1999 | Meyer et al. | |
| 6,051,581 A | 4/2000 | Gordon et al. | |
| 6,232,319 B1 | 5/2001 | Marazano et al. | |
| 6,277,870 B1 | 8/2001 | Gurley et al. | |
| 6,358,941 B1 | 3/2002 | Snorrason et al. | |
| 6,416,735 B1 | 7/2002 | Carroll et al. | |
| 6,479,510 B2 | 11/2002 | Myers et al. | |
| 6,492,385 B2 | 12/2002 | Myers et al. | |
| 6,500,840 B2 | 12/2002 | Myers et al. | |
| 6,569,865 B2 | 5/2003 | Eifion | |
| 6,780,861 B2 | 8/2004 | Nozulak | |
| 6,861,443 B2 | 3/2005 | Gurley et al. | |
| 6,869,958 B2 | 3/2005 | Li | |
| 6,875,606 B1 | 4/2005 | Leonard et al. | |
| 6,908,927 B2 | 6/2005 | Galli et al. | |
| 6,911,543 B2 | 6/2005 | Walker et al. | |
| 6,943,184 B2 | 9/2005 | Goldstein et al. | |
| 6,953,855 B2 | 10/2005 | Mazurov et al. | |
| 6,964,961 B2 | 11/2005 | Luzzio et al. | |
| 6,964,972 B2 | 11/2005 | Peters et al. | |
| 6,987,106 B1 | 1/2006 | Gallet et al. | |
| 6,995,167 B2 | 2/2006 | Loch, III et al. | |
| 7,067,261 B2 | 6/2006 | Bencherif et al. | |
| 7,067,515 B2 | 6/2006 | Wishka et al. | |
| 7,196,096 B2 | 3/2007 | Loch, III et al. | |
| 7,214,686 B2 | 5/2007 | Bencherif et al. | |
| 7,256,288 B2 | 8/2007 | Hendrix et al. | |
| 7,358,057 B2 | 4/2008 | Wang et al. | |
| 7,579,362 B2 | 8/2009 | Feuerbach et al. | |
| 7,732,477 B2 | 6/2010 | Hendrix et al. | |
| 7,767,193 B2 | 8/2010 | Mazurov et al. | |
| 7,795,453 B2 | 9/2010 | Flessner et al. | |
| 7,902,222 B2 | 3/2011 | Ji et al. | |
| 7,935,815 B2 | 5/2011 | Kimura et al. | |

(Continued)

FOREIGN PATENT DOCUMENTS

AU 200145207 6/2001
AU 2002316828 10/2002

(Continued)

OTHER PUBLICATIONS

Acker, Brad A. et al., "Discovery of N-[(3R,5R)-1-azabicyclo[3.2.1]oct-3-yl]furo[2,3-c]pyridine-5-carboxamide as an agonist of the α7 nicotinic acetylcholine receptor: In vitro and in vivo activity," *Bioorganic & Medicinal Chemistry Letters*, 18:12 (Jun. 2008) 3611-3615. et al., "Normalization of auditory physiology by cigarette smoking in schizophrenic patients," *Am J Psychiatry*, 150 (1993) 1856-1861.

Adler, et al., "Schizophrenia, sensory gating, and nicotinic receptors," *Schizophr Bull*, 24 (1998) 189-202.

Ahnallen, Christopher G. "The role of the α7 nicotinic receptor in cognitive processing of persons with schizophrenia," *Current Opinion Psychiatry*, 25:2 (Mar. 2012) 103-108.

(Continued)

*Primary Examiner* — Heidi Reese
(74) *Attorney, Agent, or Firm* — Jones Day

(57) ABSTRACT

Crystalline Forms I and II of (R)-7-chloro-N-(quinuclidin-3-yl)benzo[b]thiophene-2-carboxamide hydrochloride monohydrate and compositions, methods of manufacture and therapeutic uses thereof are described.

16 Claims, 8 Drawing Sheets

(56) References Cited

U.S. PATENT DOCUMENTS

| | | |
|---|---|---|
| 7,964,607 B2 | 6/2011 | Verhoest et al. |
| 8,076,355 B2 | 12/2011 | Hendrix et al. |
| 8,084,462 B2 | 12/2011 | Mazurov et al. |
| 8,124,618 B2 | 2/2012 | Mazurov et al. |
| 8,124,619 B2 | 2/2012 | Mazurov et al. |
| 8,124,620 B2 | 2/2012 | Mazurov et al. |
| 2002/0052389 A1 | 5/2002 | Myers et al. |
| 2003/0092613 A1 | 5/2003 | Lee et al. |
| 2003/0119840 A1 | 6/2003 | Galli et al. |
| 2004/0019053 A1 | 1/2004 | Roark |
| 2004/0039045 A1 | 2/2004 | Schiemann et al. |
| 2004/0043983 A1 | 3/2004 | Li |
| 2004/0249150 A1 | 12/2004 | Piotrowski et al. |
| 2004/0254373 A1 | 12/2004 | Piotrowski et al. |
| 2004/0266757 A1 | 12/2004 | Galli et al. |
| 2005/0004128 A1 | 1/2005 | Galli et al. |
| 2005/0020599 A1 | 1/2005 | Galli et al. |
| 2005/0031651 A1 | 2/2005 | Gervais et al. |
| 2005/0032845 A1 | 2/2005 | Goldstein et al. |
| 2005/0107460 A1 | 5/2005 | Luithle et al. |
| 2005/0119249 A1 | 6/2005 | Buntinx |
| 2005/0119325 A1 | 6/2005 | Hendrix et al. |
| 2005/0154045 A1 | 7/2005 | Luithle et al. |
| 2005/0209236 A1 | 9/2005 | Hendrix et al. |
| 2005/0245504 A1 | 11/2005 | Corbett et al. |
| 2005/0245531 A1 | 11/2005 | Ji et al. |
| 2005/0250816 A1 | 11/2005 | Piotrowski et al. |
| 2006/0160835 A1 | 7/2006 | Bencherif et al. |
| 2006/0167002 A1 | 7/2006 | Feuerbach et al. |
| 2007/0037844 A1 | 2/2007 | Luithle et al. |
| 2007/0274628 A1 | 11/2007 | Hayee et al. |
| 2009/0054446 A1 | 2/2009 | Feuerbach et al. |
| 2009/0088418 A1 | 4/2009 | Pfister et al. |
| 2009/0221555 A1 | 9/2009 | Ahmed et al. |
| 2010/0004162 A1 | 1/2010 | Heintz et al. |
| 2010/0130540 A1 | 5/2010 | Duggan |
| 2010/0190771 A1 | 7/2010 | Claffey et al. |
| 2010/0222378 A1 | 9/2010 | Hendrix et al. |
| 2010/0261752 A1 | 10/2010 | Beattie et al. |
| 2010/0324085 A1 | 12/2010 | Flessner et al. |
| 2011/0009619 A1 | 1/2011 | Kimura et al. |
| 2011/0021590 A1 | 1/2011 | Duggan |
| 2011/0065696 A1 | 3/2011 | Kimura et al. |
| 2011/0262442 A1 | 10/2011 | Hamilton et al. |
| 2011/0269764 A1 | 11/2011 | Cohen et al. |
| 2011/0274628 A1 | 11/2011 | Borschke |
| 2011/0305751 A1 | 12/2011 | Gaillard |
| 2012/0010148 A1 | 1/2012 | Gozes et al. |
| 2012/0046283 A1 | 2/2012 | Campbell et al. |
| 2012/0053171 A1 | 3/2012 | Kitazawa et al. |
| 2012/0058992 A1 | 3/2012 | Cohen et al. |
| 2012/0071483 A1 | 3/2012 | Cohen et al. |
| 2012/0202842 A1 | 8/2012 | Hendrix et al. |

FOREIGN PATENT DOCUMENTS

| | | |
|---|---|---|
| CA | 2317025 | 6/2000 |
| CA | 2393004 | 6/2001 |
| CA | 2393538 | 6/2001 |
| CA | 2460075 | 3/2003 |
| CA | 2475773 | 3/2003 |
| CA | 2464194 | 5/2003 |
| CA | 2465680 | 5/2003 |
| CA | 2466344 | 5/2003 |
| CA | 2466375 | 5/2003 |
| CA | 2476417 | 8/2003 |
| CA | 2476624 | 8/2003 |
| CA | 2476681 | 8/2003 |
| DE | 3724059 | 2/1988 |
| DE | 3740984 | 6/1989 |
| DE | 3810552 | 10/1989 |
| DE | 10044905 | 3/2002 |
| DE | 10156719 | 5/2003 |
| DE | 10162442 | 7/2003 |
| EP | 0322016 | 6/1989 |
| EP | 0327335 | 8/1989 |
| EP | 0353371 | 2/1990 |
| EP | 0405617 | 1/1991 |
| EP | 0485962 | 5/1992 |
| EP | 0512350 | 11/1992 |
| EP | 1022029 | 7/2000 |
| EP | 2002-030084 | 1/2002 |
| EP | 1219622 | 7/2002 |
| EP | 1231212 | 8/2002 |
| EP | 2277850 | 1/2011 |
| GB | 2208862 | 4/1989 |
| GB | 2231265 | 11/1990 |
| JP | 11080027 | 3/1999 |
| JP | 2002030084 | 1/2002 |
| JP | 2003081978 | 3/2003 |
| WO | WO 91/09593 | 7/1991 |
| WO | WO 93/15073 | 8/1993 |
| WO | WO 96/33186 | 10/1996 |
| WO | WO 97/30998 | 8/1997 |
| WO | WO 99/03859 | 1/1999 |
| WO | WO 99/45926 | 9/1999 |
| WO | WO 99/62505 | 12/1999 |
| WO | WO 00/10997 | 3/2000 |
| WO | WO 01/29034 | 4/2001 |
| WO | WO 01/32619 | 5/2001 |
| WO | WO 01/32620 | 5/2001 |
| WO | WO 01/32622 | 5/2001 |
| WO | WO 01/36417 | 5/2001 |
| WO | WO 01/55150 | 8/2001 |
| WO | WO 01/60821 | 8/2001 |
| WO | WO 01/66546 | 9/2001 |
| WO | WO 02/15662 | 2/2002 |
| WO | WO 02/16357 | 2/2002 |
| WO | WO 02/20016 | 3/2002 |
| WO | WO 02/44176 | 6/2002 |
| WO | WO 02/057275 | 7/2002 |
| WO | WO 02/085901 | 10/2002 |
| WO | WO 02/096912 | 12/2002 |
| WO | WO 02/100857 | 12/2002 |
| WO | WO 02/100858 | 12/2002 |
| WO | WO 03/018585 | 3/2003 |
| WO | WO 03/029252 | 4/2003 |
| WO | WO 03/037896 | 5/2003 |
| WO | WO 03/044019 | 5/2003 |
| WO | WO 03/044020 | 5/2003 |
| WO | WO 03/044024 | 5/2003 |
| WO | WO 03/051874 | 6/2003 |
| WO | WO 03/055878 | 7/2003 |
| WO | WO 03/072578 | 9/2003 |
| WO | WO 03/078430 | 9/2003 |
| WO | WO 03/078431 | 9/2003 |
| WO | WO 03/087102 | 10/2003 |
| WO | WO 03/087103 | 10/2003 |
| WO | WO 03/087104 | 10/2003 |
| WO | WO 03/091694 | 11/2003 |
| WO | WO 03/093250 | 11/2003 |
| WO | WO 03/094830 | 11/2003 |
| WO | WO 03/094831 | 11/2003 |
| WO | WO 03/104227 | 12/2003 |
| WO | WO 2004/013137 | 2/2004 |
| WO | WO 2004/016608 | 2/2004 |
| WO | WO 2004/016616 | 2/2004 |
| WO | WO 2004/016617 | 2/2004 |
| WO | WO 2004/019943 | 3/2004 |
| WO | WO 2004/019947 | 3/2004 |
| WO | WO 2004/029050 | 4/2004 |
| WO | WO 2004/039321 | 5/2004 |
| WO | WO 2004/039815 | 5/2004 |
| WO | WO 2004/043960 | 5/2004 |
| WO | WO 2004/052348 | 6/2004 |
| WO | WO 2004/052461 | 6/2004 |
| WO | WO 2004/052889 | 6/2004 |
| WO | WO 2004/052894 | 6/2004 |
| WO | WO 2004/056744 | 7/2004 |
| WO | WO 2004/064836 | 8/2004 |
| WO | WO 2004/085433 | 10/2004 |
| WO | WO 2005/012299 | 2/2005 |
| WO | WO 2005/092890 | 10/2005 |

(56) References Cited

FOREIGN PATENT DOCUMENTS

| WO | WO 2005/117890 | 12/2005 |
|---|---|---|
| WO | WO 2006/010008 | 1/2006 |
| WO | WO 2006/030031 | 3/2006 |
| WO | WO 2006/065233 | 6/2006 |
| WO | WO 2006/066879 | 6/2006 |
| WO | WO 2007/038367 | 4/2007 |
| WO | WO 2008/100867 | 8/2008 |
| WO | WO 2009/018505 | 2/2009 |
| WO | WO 2009/073788 | 6/2009 |
| WO | WO 2010/059844 | 5/2010 |
| WO | WO 2010/098488 | 9/2010 |
| WO | WO 2010/098495 | 9/2010 |
| WO | WO 2010/132423 | 11/2010 |
| WO | WO 2011/009097 | 1/2011 |
| WO | WO 2011/033018 | 3/2011 |
| WO | WO 2011/036167 | 3/2011 |
| WO | WO 2011/044264 | 4/2011 |
| WO | WO 2011/044535 | 4/2011 |
| WO | WO 2011/044537 | 4/2011 |
| WO | WO 2011/047432 | 4/2011 |
| WO | WO 2011/054759 | 5/2011 |
| WO | WO 2011/063415 | 5/2011 |
| WO | WO 2011/064288 | 6/2011 |
| WO | WO 2011/084368 | 7/2011 |
| WO | WO 2011/139811 | 11/2011 |
| WO | WO 2011/146511 | 11/2011 |
| WO | WO 2011/156640 | 12/2011 |
| WO | WO 2011/156646 | 12/2011 |
| WO | WO 2011/156775 | 12/2011 |
| WO | WO 2011/156780 | 12/2011 |
| WO | WO 2011/156786 | 12/2011 |
| WO | WO 2011/159945 | 12/2011 |

OTHER PUBLICATIONS

Adler,
Anderson et al., "Tools for Purifying the Product: Column Chromatography, Crystallization and Reslurrying," *Practical Process Research and Development*, Academic Press, San Diego (Jan. 1, 2000) 223-247.
Araki, Hiroaki et al. "Neuronal nicotinic receptor and psychiatric disorders: Functional and behavioral effects of nicotine," *Japanese J Pharmacol*, 88 (2002) 133-138.
Arendash, Gary W. et al. "Improved learning and memory in aged rats with chronic administration of the nicotinic receptor agonist GTS-21," *Brain Research*, 674 (1995) 252-259.
Baldeweg, et al. "Nicotinic modulation of human auditory sensory memory: Evidence from mismatch negativity potentials," *Int J Psychophysiol*, 59 (2006) 49-58.
Banerjee, Carolin et al. "Cellular expression of α7 nicotinic acetylcholine receptor protein in the temporal cortex in Alzheimer's and Parkinson's Disease—A stereological approach," *Neurobiology of Disease*, 7 (2000) 666-672.
Bednar, Ivan et al. "Selective nicotinic receptor consequences in $APP_{SWE}$ transgenic mice," *Molecular Cell Neurosci*, 20 (2002) 354-365.
Belluardo, N. et al. "Neurotrophic effects of central nicotinic receptor activation," *J Neural Transmission* [Supplement], 60 (2000) 227-245.
Belluardo, Natale et al. "Central nicotinic receptors, neurotrophic factors and neuroprotection," *Behavioural Brain Res*, 113 (2000) 21-34.
Bhat, B. et al., "A Novel One-Step Synthesis of 2-Methoxycarbonyl-thieno[2,3-b]quinolines and 3-Hydroxy-2-methoxwarbonyl-2,3-dihydrothieno[2,3-b]-quinolines," *Synthesis* (Aug. 1984) 673-676.
Bitner, R. Scott et al. "In vivo pharmacological characterization of a novel selective α7 neuronal nicotinic acetylcholine receptor agonist ABT-107: Preclinical considerations in Alzheimer's disease," *J Pharmacol Exp Ther*, 334:3 (2010) 875-886.
Bitner, Robert S. et al. "Broad-spectrum efficacy across cognitive domains by α7 nicotinic acetylcholine receptor agonism correlates with activation of ERK1/2 and CREB phosphorylation pathways," *J Neurosci*, 27:39 (Sep. 26, 2007) 10578-10587.
Biton, Bruno et al. "SSR180711, a novel selective α7 nicotinic receptor partial agonist: (I) Binding and functional profile," *Neuropsychopharmacology*, 32 (2007) 1-16.
Bjugstad, Kimberly B. et al. "Long-term treatment with GTS-21 or nicotine enhances water maze performance in aged rats without affecting the density of nicotinic receptor subtypes in neocortex," *Drug Dev Research*, 39 (1996) 19-28.
Blokland, A. et al., "State-dependent impairment in object recognition after hippocampal NOS inhibition," *NeuroReport*, 8:18 (Dec. 1998) 4205-4208.
Bodnar, Alice et al. "Discovery and structure—activity relationship of quinuclidine benzamides as agonists of α7 nicotinic acetylcholine receptors," *J Med Chem*, 48 (2005) 905-908.
Boess et al., "Inhibition of phosphodiesterase 2 increases neuronal cGMP, synaptic plasticity and memory performance," *Neuropharmacology*, 47 (2004) 1081-1092.
Boess, Frank G. et al. "The novel α7 nicotinic acetylcholine receptor agonist N-[(3R)-1-azabicyclo[2.2.2]oct-3-yl]-7-[2-(methoxy)phenyl]-1-benzofuran-2-carboxamide improves working and recognition memory in rodents," *J Pharmacol Exp Ther*, 321:2 (2007) 716-725.
Bogdal, D. et al., "Microwave-Assisted Preparation of Benzo[b]furans under Solventless Phase-Transfer Catalytic Conditions," *Tetrahedron*, 56 (2000) 8769-8773.
Boutros, et al. "Test-retest reliability of the P50 mid-latency auditory evoked response," *Psychiatry Res*, 39 (1991) 181-192.
Bridges, A.J. et al., "Fluorine as an Ortho-Directing Group in Aromatic Metalation: A Two Step Preparation of Substituted Benzo[b]thiophene-2-carboxylates" *Tetrahedron Letters*, 33:49 (1992) 7499-7502.
Briggs, Clark A. et al. "Functional characterization of the novel neuronal nicotinic acetylcholine receptor ligand GTS-21 in vitro and in vivo," *Pharmacol Biochem Behavior*, 57:1/2 (1997) 231-241.
Brittain, H.G., ed., "Methods for the Characterization of Polymorphs and Solvates," *Polymorphism in Pharmaceutical Solids* (Jan. 1, 1999) 227-278.
Broide, R.S. et al., "The α7 Nicotinic Acetylcholine Receptor in Neuronal Plasticity," *Molecular Neurobiology*, vol. 20 (1999) 1-16.
Buccafusco et al., "Desensitization of Nicotinic Acetylcholine Receptors as a Strategy for Drug Development," *J of Pharm. and Exp. Ther.*, 328:2 (2009) 364-370.
Byrn, S. et al. "Pharmaceutical Solids: A Strategic Approach to Regulatory Considerations," *Pharmaceutical Research*, Kluwer Academic Publishers, New York, 12:7 (Jul. 1, 1995) 945-954.
Caira, M.R. "Crystalline Polymorphism of Organic Compounds," *Topics in Current Chemistry*, vol. 198 (Jan. 1, 1998) 163-208.
Chen, Y. et al. "Nicotine and an α7 selective nicotinic agonist AR-R17779 facilitate the induction of long-term potentiation induced by a short tetanus," *Soc Neuroscience*, Program No. 420.3 (Nov. 7, 2000). (Abstract only).
Krutcher, Keith A. "GTS-21" *Current Opinion in Central Peripheral Nervous System Investigational Drugs*, 2:4 (2000) 478-484.
Cummings, J. L. "Cholinesterase inhibitors: A new class of psychotropic compounds," *American Journal of Psychiatry*, 157:1 (Jan. 2000) 4-15.
D'Andrea, Michael R. et al. "Targeting intracellular Aβ42 for Alzheimer's Disease drug discovery," *Drug Dev Research*, 56 (2002) 194-200.
Dalebout, et al. "Reliability of the mismatch negativity in the responses of individual listeners," *J Am Acad Audiol*, 12 (2001) 245-253.
Dance, Amber et al. "The society for neuroscience 2009 meeting report, part 2," *J Alzheimers Disease*, 19 (2010) 1409-1415.
Davies, A.R.L. et al., "Characterisation of the binding of [$^3$H]methyllycaconitine: a new radioligand for labelling α7-type neuronal nicotinic acetylcholine receptors" *Neuropharmacology*, 38 (1999) 679-690.
De Bruin et al., "SLV330: A cannabinoid CB1 receptor antagonist, ameliorates deficits in the T-maze, object recognition and social recognition tasks in rodents," *Neurobiol Learn Mem*, 93 (2010) 522-531.

(56) References Cited

OTHER PUBLICATIONS

De Strooper, Bart et al. "The secretases: Enzymes with therapeutic potential in Alzheimer disease," *Nature Rev: Neurol*, 6 (Feb. 2010) 99-107.

De Wilde, et al., "A meta-analysis of P50 studies in patients with schizophrenia and relatives: differences in methodology between research groups," *Schizophr Res*, 97 (2007) 137-151.

Dierks, et al., "Event-related potentials and psychopharmacology: Cholinergic modulation of P300," *Pharmacopsychiatry*, 27 (1994) 72-74.

Dunbar, et al., "Effects of TC-1734 (AZD3480), a selective neuronal nicotinic receptor agonist, on cognitive performance and the EEG of young healthy male volunteers," *Psychopharmacology* (Berl), 191 (2007) 919-929.

Duncan et al., "Effects of smoking on acoustic startle and prepulse inhibition in humans," *Psychopharmacology* (Berl), 156 (2001) 266-272.

Easton, et al., "Beneficial effects of thiamine on recognition memory and P300 in abstinent cocaine-dependent patients," *Psychiatry Res*, 70 (1997) 165-174.

Ennaceur et al., "A new one-trial test for neurobiological studies of memory in rats. II: Effects of piracetam and pramiracetam," *Behav Brain Res*, 33 (1989) 197-207.

Ennaceur, A. et al., "A new one-trial test for neurobiological studies of memory in rats. 1: Behavioral data," *Behavioural Brain Research*, vol. 31 (1988) 47-59.

Ennaceur, A. et al., "Effects of physostigmine and scopolamine on rats' performances in object-recognition and radial-maze tests," *Psychopharmacology*, vol. 109 (1992) 321-330.

Feuerbach, D. et al. "The selective nicotinic acetylcholine receptor alpha7 agonist JN403 is active in animal models of cognition, sensory gating, epilepsy and pain," *Neuropharmacology*, 56:1 (Jan. 1, 2009) 254-263.

Folstein, Marshal et al., "'Mini-Mental State': A Practical Method for Grading the Cognitive State of Patients for the Clinician," *Journal of Psychiatric Research*, 12 (1975) 189-98.

Freedman et al., "Linkage disequilibrium for schizophrenia at the chromosome 15q13-14 locus of the α7-nicotinic acetylcholine receptor subunit gene (CHRNA7)," *Am J Med Genet*, 105 (2001) 20-22.

Freedman, Robert et al. "Initial phase 2 trial of a nicotinic agonist in schizophrenia," *Am J Psychiatry*, 165 (2008) 1040-1047.

Fuerst et al., "Range of sensory gating values and test-retest reliability in normal subjects," *Psychophysiology*, 44 (2007) 620-626.

Galasko, Douglas et al., "An Inventory to Assess Activities of Daily Living for Clinical Trials in Alzheimer's Disease," *Alzheimer Disease and Associated Disorders*, 11:S2 (1997) S33-S39.

Galzi, J.L. et al., "Neuronal Nicotinic Receptors: Molecular Organization and Regulations," *Neuropharmacology*, 34:6 (1995) 563-582.

George, Tony et al. "Nicotinic modulation of mesoprefrontal dopamine neurons: Pharmacologic and neuroanatomic characterization," *J Pharmacol Exp Ther*, 295:1 (2000) 58-66.

Gray, J.A. et al. "The pipeline and future of drug development in schizophrenia," *Molecular Psychiatry*, 12:10 (Oct. 2007) 904-922.

Gray, Richard et al. "Hippcampal synaptic transmission enhanced by low concentrations of nicotine," *Nature*, 383 (Oct. 1996) 713-716.

Guillory, J. K. "Generation of Polymorphs, Hydrates, Solvates and Amorphous Solids," *Polymorphism in Pharmaceutical Solids* (Jan. 1, 1999) 183-226.

Harwood, L. M. et al. "Experimental organic chemistry—Principles and Practice," *Experimental Chemistry—Organic Chemistry and Reaction* (Jan. 1, 1989) 127-132.

Hauser, T.A. et al. "TC-5619: An alpha7 neuronal nicotinic receptor-selective agonist that demonstrates efficacy in animal models of the positive and negative symptoms and cognitive dysfunction of schizophrenia," *Biochemical Pharmacology*, 78:7 (Oct. 1, 2009) 803-812.

Haydar, Simon N. et al. "Neuronal nicotinic acetylcholine receptors—Targets for the development of drugs to treat cognitive impairment associated with schizophrenia and Alzheimer's disease," *Curr Topics Med Chem*, 10 (2010) 144-152.

Heinrichs, R.W., "Meta-analysis and the science of schizophrenia: variant evidence or evidence of variants?" *Neurosci Biobehav Rev*, 28 (2004) 379-394.

Ho, Yuan-Soon et al. "The alpha-9 nicotinic acetylcholine receptor serves as a molecular target for breast cancer therapy," *J Exp Clin Med*, 3:6 (2011) 246-251.

Huang, Mei et al. "The alpha-7 receptor agonist EVP-6124 increases dopamine and glutamate efflux in rat medial prefrontal cortex and nucleus accumbens," *Biochem Pharmacol*, 82:2.13 (2011) 1040 (Abstract only).

Hughes, Charles P. et al., "A New Clinical Scale for the Staging of Dementia," *Brit. J. Psychiat.*, 140 (1982) 566-572.

Ishikawa, Masatomo et al. "α7 Nicotinic acetylcholine receptor as a potential therapeutic target for schizophrenia," *Curr Pharmaceut Design*, 17 (2011) 121-129.

Ji, Daoyun et al. "Timing and location of nicotinic activity enhances or depresses hippocampal synaptic plasticity," *Neuron*, 31 (Jul. 2001) 131-141.

Kaga et al., "Cat P300 and cholinergic septohippocampal neurons: depth recordings, lesions, and choline acetyltransferase immunohistochemistry," *Neurosci Res*, 13 (1992) 53-71.

Katada et al., "Long-term effects of donepezil on P300 auditory event-related potentials in patients with Alzheimer's disease," *J Geriatr Psychiatry Neurol*, 16 (2003) 39-43.

Kawamata, Jun et al. "Stimulating nicotinic receptors trigger multiple pathways attenuating cytotoxicity in models of Alzheimer's and Parkinson's diseases," *J Alzheimers Disease*, 24 (2011) 95-109.

Kern, William R. "The brain α7 nicotinic receptor may be an important therapeutic target for the treatment of Alzheimer's Disease: Studies with DMXBA (GTS-21)," *Behavioural Brain Res*, 113 (2000) 169-181.

Kem, William R. et al. "Hydroxy metabolites of the Alzheimer's drug candidate 3-[(2,4-dimethoxy)benzylidene]-anabaseine dihydrochloride (GTS-21): Their molecular properties, interactions with brain nicotinic receptors, and brain penetration," *Mol Pharmacol*, 65:1 (2004) 56-67.

Kitagawa, Harumi et al. "Safety, pharmacokinetics, and effects on cognitive function of multiple doses of GTS-21 in healthy male volunteers," *Neuropsychopharmacology*, 28 (2003) 542-551.

Koenig, G. et al. "EVP-6124, a novel and potent α7 nicotinic acetylcholine receptor agonist, improves memory acquisition, retention and retrieval and reverses scopolamine-induced memory deficits," *Soc Neuroscience*, Abst 887.6/FF136 (Oct. 21, 2009) 1-4.

Lanctôt, Krista L. et al. "Therapy for Alzheimer's disease: How effective are current treatments?" *Therapeut Adv Neurol Disorders*, 2:3 (2009) 163-180.

Levin, E. D. et al. "AR-R17779, an α7 nicotinic agonist, improves memory and learning in rats," *Behavioural Pharmacol*, 10 (1999) 675-780.

Levin, Edward D. et al. "Development of nicotinic drug therapy for cognitive disorders," *Euro J Pharmacol*, 393 (2000) 141-146.

Levin, Edward et al. "Nicotinic treatment for cognitive dysfunction," *Curr Drug Targets—CNS & Neurol Disord*, 1 (2002) 423-431.

Levin, Edward, "Nicotinic receptor subtypes and cognitive function," *J Neurobiology* 53 (2002) 633-640.

Li, X. D. et al. "Blood pressure and heart rate responses to central injection of choline: Role of α7-nicotinic cholinergic receptors," *Soc Neuroscience*, Program No. 136.6 (Nov. 3, 2002).(Abstract only).

Liu, Qing-song et al. "β-Amyloid peptide blocks the response of α7-containing nicotinic receptors on hippocampal neurons," *Proc Natl Acad Sci*, 98:8 (2001) 4734-4739.

Malysz, John et al. "In vitro pharmacological characterization of a novel selective α7 neuronal nicotinic acetylcholine receptor agonist ABT-107," *J Pharmacol Exp Ther*, 334:3 (2010) 863-874.

Mancuso, Cesare et al. "Pharmacologists and Alzheimer disease therapy: to boldly go where no scientist has gone before," *Expert Opin Invest Drugs*, 20:9 (2011) 1243-1261.

Mangialasche, Francesca et al. "Alzheimer's Disease: clinical trials and drug development," *Lancet Neurology*, 9 (2010) 702-716.

Maurer et al., "The relationship between the exposure and nonspecific binding of thirty-three central nervous system drugs in mice," *Drug Metabolism and Disposition*, 33 (2005) 175-181.

(56) References Cited

OTHER PUBLICATIONS

Mazarov, Anatoly A. et al. "Discovery and development of α7 nicotinic acetylcholine receptor modulators," *J Med Chem*, 54 (2011) 7943-7961.

McGehee, D.S. et al., "Physiological Diversity of Nicotinic Acetylcholine Receptors Expressed by Vertebrate Neurons," *Annu. Rev. Physiol.*, vol. 57 (1995) 521-546.

Meyer, Edwin M. et al. "3-[2,4-Dimethoxybenzylidene]anabaseine (DMXB) selectively activates rat α7 receptors and improves memory-related behaviors in a mecamylamine-sensitive manner," *Brain Research*, 768 (1997) 49-56.

Meyer, Edwin M. et al. "Analysis of 3-(4-hydroxy, 2-methoxybenzylidene)anabaseine selectivity and activity at human and rat α7 nicotinic receptors," *J Pharmacol Exp Ther*, 287 (1998) 918-925.

Meyer, Edwin M. et al. "Neuroprotective and memory-related actions of novel α7 nicotinic agents with different mixed agonist/antagonist properties," *J Pharmacol Exp Ther*, 284:3 (1998) 1026-1032.

Mimica, Ninoslav et al. "Current treatment options for people with Alzheimer's disease in Croatia," *Chemico-Biological Interactions*, 187 (2010) 409-410.

Mohs, Richard C. et al., "Development of Cognitive Instruments for Use in Clinical Trials of Antidementia Drugs: Additions to the Alzheimer's Disease Assessment Scale That Broaden Its Scope," *Alzheimer's Disease and Associated Disorders*, 11:S2 (1997) S13-S21.

Naatanen et al., "Generators of electrical and magnetic mismatch responses in humans," *Brain Topogr*, 7 (1995) 315-320.

Ng, Herman J. et al. "Nootropic α7 nicotinic receptor allosteric modulator derived from $GABA_A$ receptor modulators," *Proc Natl Acad Sci*, 104:19 (2007) 8059-8064.

Nishizaki, Tomoyuki et al. "Presynaptic nicotinic acetylcholine receptors as a functional target of Nefiracetam in inducing a long-lasting facilitation of hippocampal neurotransmission," *Alzheimer Disease Assoc Disord*, 14:Suppl 1 (2000) s82-s94.

Nishizaki, Tomoyuki et al. "The anti-dementia drug nefiracetam facilitates hippcampal synaptic transmission by functionally targeting presynaptic nicotinic ACh receptors," *Mol Brain Res*, 80 (2000) 53-62.

Nordberg et al., "Cholinesterase Inhibitors in the Treatment of Alzheimer's Disease," *Drug Safety*, 19:6 (Dec. 1998) 465-480.

Nordberg, Agneta "Neuroprotection in Alzheimer's Disease—New strategies for treatment," *Neurotoxicity Research*, 2 (2000) 157-165.

Numata, Atsushi, "1-Azabicycloalkane Compound and Pharmaceutical Use Thereof," *Patent Abstracts of Japan*, vol. 5 (May 3, 2002) and JP 2002 030084 (Jan. 29, 2002).

O'Neill, M.J. et al. "The role of neuronal nicotinic acetylcholine receptors in acute and chronic neurodegeneration," *Curr Drug Targets—CNS & Neurol Disord*, 1 (2002) 399-411.

Olincy et al., "Proof-of-concept trial of an alpha7 nicotinic agonist in schizophrenia," *Arch Gen Psychiatry*, 63 (2006) 630-638.

Papke, Roger L. et al. "Electrophysiological perspectives on the therapeutic use of nicotinic acetylcholine receptor partial agonists," *J Pharmacol Exp Ther*, 337:2 (2011) 367-379.

Papke, Roger L. et al. "α7 Receptor-selective agonists and modes of α7 receptor activation," *Euro J Pharmacol*, 393 (2000) 179-195.

Pichat, Philippe et al. "SSR180711, a novel selective α7 nicotinic receptor partial agonist: (II) Efficacy in experimental models predictive of activity against cognitive symptoms of schizophrenia," *Neuropsychopharmacology*, 32 (2007) 17-34.

Plath, Niels et al. "Can small molecules provide truly effective enhancement of cognition? Current achievements and future directions," *Expert Opin Invest Drugs*, 20:6 (2011) 795-811.

Potter et al., "Review of clinical correlates of P50 sensory gating abnormalities in patients with schizophrenia," *Schizophr Bull*, 32 (2006) 692-700.

Prickaerts et al., "Dissociable effects of acetylcholinesterase inhibitors and phosphodiesterase type 5 inhibitors on object recognition memory: acquisition versus consolidation," *Psychopharmacology*, 177 (2005) 381-390.

Prickaerts et al., "Phosphodiesterase type 5 inhibition improves early memory consolidation of object information," *Neurochem Int*, 45 (2004) 915-928.

Prickaerts, J. et al., "Possible role of nitric oxide-cyclic GMP pathway in object recognition memory: Effects of 7-nitroindazole and zaprinast", *European Journal of Pharmacology*, 337 (1997) 125-136.

Prickaerts, Jos et al. "EVP-6124, a novel and selective α7 nicotinic acetylcholine receptor partial agonist, improves memory performance by potentiating the acetylcholine response of α7 nicotinic acetylcholine receptors," *Neuropharmacology*, 62 (2012) 1099-1110.

Rezvani, A.H. et al., "Effect of R3487/MEM3454, a novel nicotinic alpha7 receptor partial agonist and 5-HT3 antagonist on sustained attention in rats," *Progress in Neuro-Psychopharmacology & Biological Psychiatry*, 33:2 (Mar. 17, 2009) 269-275.

Rezvani, Amir H. et al. "Cognitive effects of nicotine," *Biological Psychiatry*, 49 (2001) 258-267.

Rosen, Wilma G. et al., "A New Rating Scale for Alzheimer's Disease," *Am J Psychiatry*, 141:11 (Nov. 1984) 1356-1364.

Rosse, Richard B. et al. "Adjuvant Galantamine administration improves negative symptoms in a patient with treatment-refractory schizophrenia," *Clin Neuropharmacol*, 25 (2002) 272-275.

Sabbagh et al., "Drug development for Alzheimer's disease: Where are we now and where are we headed?" *American Journal of Geriatric Pharmacotherapy, Excerpta Medica*, 7:3 (Jun. 1, 2009) 167-185.

Sandman et al., "The auditory event-related potential is a stable and reliable measure in elderly subjects over a 3 year period," *Clin Neurophysiol*, 111 (2000) 1427-1437.

Schall et al., "Functional neuroanatomy of auditory mismatch processing: an event-related fMRI study of duration deviant oddballs," *Neuroimage*, 20 (2003) 729-736.

Seguela, P. et al., "Molecular Cloning, Functional Properties, and Distribution of Rat Brain α7: A Nicotinic Cation Channel Highly Permeable to Calcium," *Journal of Neuroscience*, 13:2 (Feb. 1993) 596-604.

Silva, Alcino J. et al. "Molecular and cellular mechanisms of cognitive function: Implications for psychiatric disorders," *Biological Psychiatry*, 47 (2000) 200-209.

Smulders, Chantal J.G.M. et al. "Cholinergic drugs potentiate human nicotinic α4β2 acetylcholine receptors by a competitive mechanism," *Euro J Pharmacol*, 509 (2005) 97-108.

Stahl, Stephen M., Ph.D. "Paying Attention to Your Acetylcholine, Part 2: The function of nicotinic receptors," *J Clin Psychiatry*, 61:9 (Sep. 2000) 628-629.

Strobel, Gabrielle "12th International Conference on Alzheimer's Disease (ICAD), Vienna, Austria," *J Alzheimers Disease*, 18 (2009) 973-990.

Sydserff, Simon et al. "Selective α7 nicotinic receptor activation by AZD0328 enhances cortical dopamine release and improves learning and attentional processes," *Biochem Pharmacol*, 78 (2009) 880-888.

Taly, Antoine et al. "Nicotinic receptors: Allosteric transitions and therapeutic targets in the nervous system," *Nature Rev: Drug Discovery*, 8 (Sep. 2009) 733-750.

Tcheremissine, Oleg V. et al. "Targeting cognitive deficits in schizophrenia: A review of the development of a new class of medicines from the perspective of community mental health researchers," *Expert Opin Invest Drugs*, 21:1 (2012) 7-14.

Thomsen, Morten S. et al. "Cognitive improvement by activation of α7 nicotinic acetylcholine receptors: From animal models to human pathophysiology," *Curr Pharmaceut Design*, 16 (2010) 323-343.

Townsend, Matthew "When will Alzheimer's Disease be cured? A pharmaceutical perspective," *J Alzheimers Disease*, 24 (2011) 43-52.

Trainor et al., "The importance of plasma protein binding in drug discovery," *Expert Opinion in Drug Discovery*, 20 (2007) 51-64.

Turetsky et al., "Neurophysiological endophenotypes of schizophrenia: the viability of selected candidate measures," *Schizophr Bull*, 33 (2007) 69-94.

(56) References Cited

OTHER PUBLICATIONS

Umbricht et al., "Mismatch negativity in schizophrenia: a meta-analysis," *Schizophr Res*, 76 (2005) 1-23.

Upadhyaya, Prerna et al. "Therapy of Alzheimer's Disease: An update," *African J Pharm Pharmacol*, 4:6 (Jun. 2010) 408-421.

Uteshev, V. V. et al. "Kinetic analysis of α7 nAChR fast desensitization in acutely dissociated neurons: Implications for therapeutics," *Soc Neuroscience*, Program No. 716.20 (Nov. 8, 2000).(Abstract only).

van Kampen, Marja et al. "AR-R17779 improves social recognition in rats by activation of nicotinic α7 receptors," *Psychopharmacology*, 172 (2004) 375-383.

Vaucher, E. et al. "Object recognition memory and cholinergic parameters in mice expressing human presenilin 1 transgenes," *Experimental Neurology*, 175 (2002) 398-406.

Vazquez, Raymond W. et al. "Identification of a new amino acid residue capable of modulating agonist efficacy at the homomeric nicotinic acetylcholine receptor, α7," *Molecular Pharmacol*, 55 (1999) 1-7.

Vippagunta, S.R. et al., "Crystalline Solids," *Advanced Drug Delivery Reviews*, 48 (2001) 3-26.

Wallace, T. L. et al., "R3487/MEM 3454, a novel nicotinic alpha 7 receptor partial agonist, improves attention and working memory performance in cynomolgus macaques," *Biochemical Pharmacology*, 78:7 (Oct. 1, 2009) 912.

Wallace, Tanya L. et al. "Drug targets for cognitive enhancement in neuropsychiatric disorders," *Pharmacol Biochem Behavior*, 99 (2011) 130-145.

Wallace, Tanya L. et al. "RG3487, a novel nicotinic α7 receptor partial agonist, improves cognition and sensorimotor gating in rodents," *J Pharmacol Exp Ther*, 336:1 (2011) 242-253.

Wallace, Tanya L. et al. "Targeting the nicotinic alpha7 acetylcholine receptor to enhance cognition in disease," *Biochem Pharmacol*, 82 (2011) 891-903.

Werber et al., "Evaluation of cholinergic treatment in demented patients by P300 evoked related potentials," *Neurol Neurochir Pol*, 35:Suppl 3 (2001) 37-43.

Werkheiser, J. L. et al. "Ultra-low exposure to alpha-7 nicotinic acetylcholine receptor partial agonists elicits an improvement in cognition that corresponds with an increase in alpha-7 receptor expression in rodents: Implications for low dose clinical efficacy," *Neuroscience*, 186 (2011) 76-87.

Wevers, A. et al. "Expression of nicotinic acetylcholine receptor subunits in the cerebral cortex in Alzheimer's disease: histotopographical correlation with amyloid plaques and hyperphosphorylated-tau protein," *Euro J Neuroscience*, 11 (1999) 2551-2565.

Whitehead et al., "Donepezil for the Symptomatic Treatment of Patients with Mild to Moderate Alzheimer's Disease: a Meta-Analysis of Individual Patient Data from Randomised Controlled Trials," *Int J Geriatr Psychiatry*, 19 (2004) 624-633.

Wirowski, D. et al. "Expression of α4 and α7 nicotinic receptor subunits in the temporal cortex in dementia with lewy bodies and controls," *Soc Neuroscience*, Program No. 195.18 (Nov. 11, 2001). (Abstract only).

Wishka, Donn G. et al., "Discovery of $N$-[(3R)-1-azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure—Activity Relationship," *Journal of Medicinal Chemistry*, 49:14 (Jul. 2006) 4425-4436.

Woodruff-Pak, Diana "Preclinical experiments on cognition enhancement in Alzheimer's Disease: Drugs affecting nicotinic acetylcholine receptors," *Drug Dev Research*, 56 (2002) 335-346.

International Search Report mailed Jul. 21, 2011 for corresponding PCT/US2011/036844.

Ivanisevic, Igor et al., "Uses of X-Ray Powder Diffraction in the Pharmaceutical Industry," *Pharmaceutical Formulation and Quality* (Aug./Sep. 2011) 32-33.

Brittain, H., ed., *Polymorphism in Pharmaceutical Solids, $2^{nd}$ Edition* (2009) 318-335.

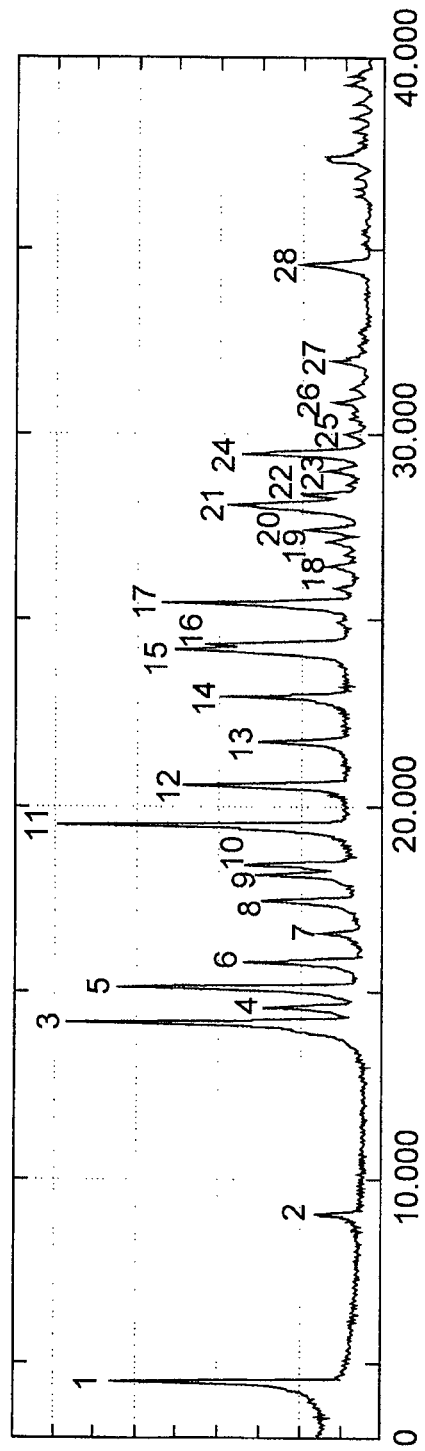

| NO. | 2θ | RELATIVE INTENSITY | NO. | 2θ | RELATIVE INTENSITY |
|---|---|---|---|---|---|
| 1 | 4.50 | 77 | 16 | 24.36 | 56 |
| 2 | 9.04 | 21 | 17 | 25.46 | 68 |
| 3 | 14.20 | 98 | 18 | 26.44 | 18 |
| 4 | 14.60 | 38 | 19 | 27.10 | 19 |
| 5 | 15.14 | 83 | 20 | 27.42 | 24 |
| 6 | 15.80 | 42 | 21 | 28.10 | 49 |
| 7 | 16.60 | 19 | 22 | 28.36 | 25 |
| 8 | 17.48 | 39 | 23 | 29.02 | 18 |
| 9 | 18.16 | 39 | 24 | 29.48 | 42 |
| 10 | 18.44 | 43 | 25 | 29.98 | 13 |
| 11 | 19.48 | 100 | 26 | 30.86 | 16 |
| 12 | 20.58 | 62 | 27 | 31.96 | 17 |
| 13 | 21.74 | 39 | 28 | 34.56 | 26 |
| 14 | 22.94 | 51 | | | |
| 15 | 24.20 | 65 | | | |

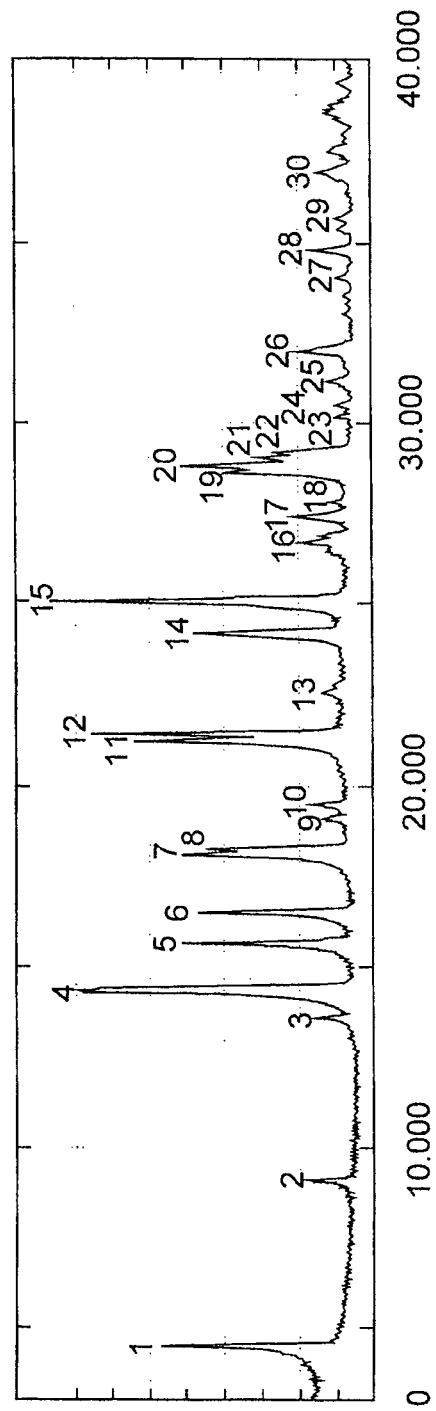

FIG. 6B

| NO. | 2θ | RELATIVE INTENSITY | NO. | 2θ | RELATIVE INTENSITY |
|---|---|---|---|---|---|
| 1 | 4.48 | 67 | 16 | 26.58 | 21 |
| 2 | 9.00 | 21 | 17 | 27.30 | 22 |
| 3 | 13.58 | 17 | 18 | 27.66 | 12 |
| 4 | 14.34 | 92 | 19 | 28.50 | 45 |
| 5 | 15.62 | 60 | 20 | 28.70 | 56 |
| 6 | 16.48 | 55 | 21 | 28.92 | 35 |
| 7 | 18.06 | 60 | 22 | 29.04 | 29 |
| 8 | 18.20 | 52 | 23 | 30.04 | 9 |
| 9 | 19.02 | 15 | 24 | 30.98 | 10 |
| 10 | 19.44 | 19 | 25 | 30.34 | 12 |
| 11 | 21.16 | 74 | 26 | 31.82 | 21 |
| 12 | 21.38 | 88 | 27 | 33.82 | 9 |
| 13 | 22.46 | 15 | 28 | 34.58 | 16 |
| 14 | 24.10 | 54 | 29 | 35.46 | 10 |
| 15 | 25.00 | 100 | 30 | 36.74 | 15 |

2θ(°)

CRYSTALLINE FORM OF (R)-7-CHLORO-N-(QUINUCLIDIN-3-YL)BENZO[B]THIOPHENE-2-CARBOXAMIDE HYDROCHLORIDE

CROSS-REFERENCE TO RELATED APPLICATIONS

This application is a continuation of U.S. application Ser. No. 13/698,759, filed Apr. 3, 2013, which is the National Phase of International Application No. PCT/US2011/036844, filed May 17, 2011, which designated the United States and was published in English, and further claims the benefit of both U.S. Provisional Application No. 61/352,092, filed Jun. 7, 2010, and U.S. Provisional Application No. 61/345,363, filed May 17, 2010. The foregoing related applications, in their entirety, are incorporated herein by reference.

FIELD OF THE INVENTION

The present disclosure relates to crystalline forms of (R)-7-chloro-N-(quinuclidin-3-yl)benzo[b]thiophene-2-carboxamide hydrochloride monohydrate and compositions, methods of manufacture and therapeutic uses thereof.

BACKGROUND OF THE INVENTION

The endogenous neurotransmitter acetylcholine (Ach) mediates diverse physiological functions in the peripheral and central nervous systems (CNS) via muscarinic and nicotinic subclasses of acetylcholine receptors (AChRs). The nicotinic acetylcholine receptors (nAChRs) are ligand-gated cell surface ion channels that are selectively activated by the natural product nicotine. The diverse molecular subtypes or variants of nicotinic acetylcholine receptor are based on the pentameric structure of the receptor. The nAChR subtypes are formed from diverse pentameric combinations of nine molecularly distinct alpha subunits and four molecularly distinct beta subunits. A particularly interesting molecular target for therapeutic intervention is the alpha-7 nicotinic receptor subtype, which is comprised of five alpha-7 monomeric subunits. Thus, agonists which are selective for the alpha-7 receptor have potential to treat a range of diseases. Alpha-7 agonists are expected to be especially useful for the treatment of CNS disorders associated with cognitive deficits. This expectation is based on beneficial effects of alpha-7 receptor activation on cognition, learning and memory. At the same time, selective alpha-7 agonists are expected to cause fewer or less severe undesirable side effects, e.g. nausea, vomiting, tachycardia, which are mediated by the activation of certain other nicotinic receptor subtypes as for example by the non-selective agonist nicotine.

As such, there is a need for additional selective alpha-7 agonists for the treatment of CNS disorders associated with cognitive deficits.

SUMMARY OF THE INVENTION

Accordingly, the present invention is directed to novel crystalline compounds for use in the treatment of CNS disorders associated with cognitive deficits. In particular, the invention provides crystalline forms, i.e., Form I and Form II, of (R)-7-chloro-N-(quinuclidin-3-yl)benzo[b]thiophene-2-carboxamide hydrochloride monohydrate having the following formula.

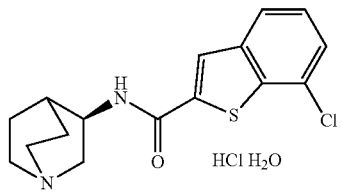

The invention further provides (a) pharmaceutical compositions comprising one of the crystalline forms, (b) methods for the treatment and/or prophylaxis of a condition in which administration of an α7 nicotinic receptor agonist may be expected to be therapeutic using one of the crystalline forms, and (c) methods of manufacturing one of the crystalline forms.

BRIEF DESCRIPTION OF THE DRAWINGS

FIGS. 5A and 5B depict an X-ray powder diffraction (XRPD) spectrum for Form I.

FIGS. 6A and 6B depict an X-ray powder diffraction (XRPD) spectrum for Form II.

DETAILED DESCRIPTION OF THE INVENTION

Figure 1:
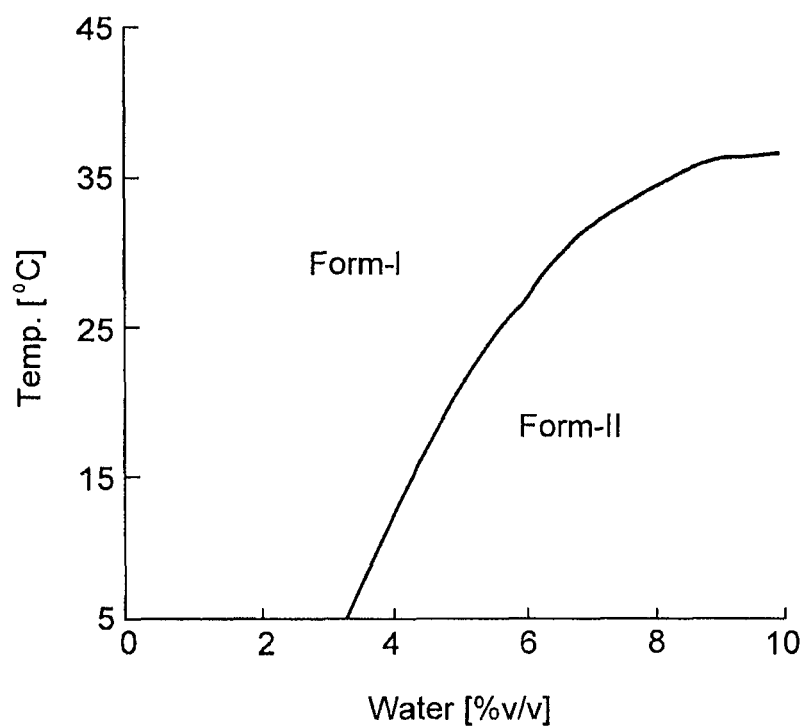
FIG. 1 is a phase diagram for Form I and Form II.

The present invention, including crystalline forms, methods, and pharmaceutical compositions will be described with reference to the following definitions that, for convenience, are set forth below. Unless otherwise specified, the below terms used herein are defined as follows.

I. Definitions

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In one embodiment, the crystalline forms of the invention are monohydrates. In certain embodiments, a crystalline form is substantially pure, isolated or enriched in one crystalline form, and/or is substantially free of amorphous forms and/or other crystal forms.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21.sup.st edition, Lippincott, Williams and Wilkins, Baltimore, Md. (2005); The United States Pharmacopeia, 23.sup.rd ed., 1843-1844 (1995).

Moreover, more detailed characterizations techniques for characterizing crystal forms and amorphous forms may include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder. Furthermore, it would be understood by the ordinarily skilled artisan that identification of a crystal may be made using one of these techniques, e.g., X-ray powder diffractometry, and may be confirmed using additional noted characterization techniques.

As used herein and unless otherwise specified, a sample comprising a particular crystal form or amorphous form that is "substantially pure," contains the particular crystal form or amorphous form in a chemical and/or physical purity greater than about 75%, e.g., 80%, e.g., 85%, e.g., 90%, e.g., 91%, e.g., 92%, e.g., 93%, e.g., 94%, e.g., 95%, e.g., 96%, e.g., 97%, e.g., 98%, e.g., 99%, e.g., 99.25%, e.g., 99.50%, e.g., 99.75%, e.g., 99.9%, e.g., 100% physically and/or chemically pure. In certain embodiments, the particular crystal form or amorphous form is greater than about 90%, e.g., 91%, e.g., 92%, e.g., 93%, e.g., 94%, e.g., 95%, e.g., 96%, e.g., 97%, e.g., 98%, e.g., 99%, e.g., 99.25%, e.g., 99.50%, e.g., 99.75%, e.g., 99.9%, e.g., 100% physically and/or chemically pure. In particular embodiments, the particular crystal form or amorphous form is greater than about 95%, e.g., 96%, e.g., 97%, e.g., 98%, e.g., 99%, e.g., 99.25%, e.g., 99.50%, e.g., 99.75%, e.g., 99.9%, e.g., 100% physically and/or chemically pure. In specific embodiments, the particular crystal form or amorphous form is greater than about 99%, e.g., 99.25%, e.g., 99.50%, e.g., 99.75%, e.g., 99.9%, e.g., 100% physically and/or chemically pure.

As used herein and unless otherwise specified, a sample or composition that is "substantially free" of one or more other solid forms and/or other chemical compounds means that the composition contains, in particular embodiments, less than about 25%, e.g., 20%, e.g., 15%, e.g., 10%, e.g., 9%, e.g., 8%, e.g., 7%, e.g., 6%, e.g., 5%, e.g., 4%, e.g., 3%, e.g., 2%, e.g., 1%, e.g., 0.75%, e.g., 0.5%, e.g., 0.25%, e.g., or 0.1% percent by weight of one or more amorphous forms and/or other crystal forms. In certain embodiments, the composition contains less than 10%, e.g., 9%, e.g., 8%, e.g., 7%, e.g., 6%, e.g., 5%, e.g., 4%, e.g., 3%, e.g., 2%, e.g., 1%, e.g., 0.75%, e.g., 0.5%, e.g., 0.25%, e.g., or 0.1% percent by weight of one or more amorphous forms and/or other crystal forms. In particular embodiments, the composition contains less than 5%, e.g., 4%, e.g., 3%, e.g., 2%, e.g., 1%, e.g., 0.75%, e.g., 0.5%, e.g., 0.25%, e.g., or 0.1% percent by weight of one or more amorphous forms and/or other crystal forms. In specific embodiments, the composition contains less than 1%, e.g., 0.75%, e.g., 0.5%, e.g., 0.25%, e.g., or 0.1% percent by weight of one or more amorphous forms and/or other crystal forms. In certain embodiments, a crystal form of a substance may be physically and/or chemically pure.

As used herein and unless otherwise specified, the terms "polymorphs," "polymorphic forms" and related terms herein, refer to two or more crystal forms that consist essentially of the same molecule, molecules, and/or ions. Different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition.

As used herein and unless otherwise specified, the term "amorphous," "amorphous form," and related terms used herein, describe that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance be about 99%, 98%, 97%, 96%, 95%, 94%, 93%, 92%, 91% or 90% physically and/or chemically pure.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the advancement or worsening of the disease or disorder resulting from the administration of a compound of the invention to a patient with such a disease or disorder. In some embodiments, the terms refer to the administration of a compound provided herein, with or without other additional active agents, after the onset of symptoms of the particular disease. The terms "treating", "treatment", or the like, as used herein covers the treatment of a disease-state in a subject, e.g., a mammal, and includes at least one of: (i) inhibiting the disease-state, i.e., partially or completely arresting its development; (ii) relieving the disease-state, i.e., causing regression of symptoms of the disease-state, or ameliorating a symptom of the disease; and (iii) reversal or regression of the disease-state, preferably eliminating or curing of the disease. In a particular embodiment the terms "treating", "treatment", or the like, covers the treatment of a disease-state in a mammal, e.g., a primate, e.g., a human, and includes at least one of (i), (ii) and (iii) above. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the administration of a compound provided herein to a subject, with or without other additional active compound, prior to the onset of symptoms, particularly to patients at risk of diseases or disorders provided herein. The terms encompass the inhibition or reduction of a symptom of the particular disease. Subjects with familial history of a disease in particular are candidates for preventive regimens in certain embodiments. In addition, subjects who have a history of recurring symptoms are also potential candidates for the prevention. In this regard, the term "prevention" may be interchangeably used with the term "prophylactic treatment." In certain embodiments, the prevention is achieved by administration of a prophylactically effective amount of a compound of the invention.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. The term "pharmaceutical composition" encompasses compositions containing a compound of the invention, e.g., crystal Form I or II, and a pharmaceutically acceptable carrier. A "pharmaceutically acceptable carrier" is a diluent, excipient or carrier that is compatible with the other ingredients of the formulation and not deleterious to the recipient thereof.

II. Compounds of the Invention

In one embodiment, the invention provides crystalline Form I and Form II of (R)-7-chloro-N-(quinuclidin-3-yl) benzo[b]thiophene-2-carboxamide hydrochloride monohydrate having the following formula.

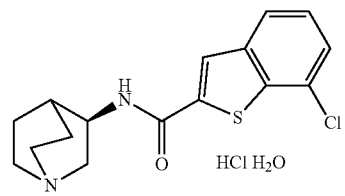

For clarity, the alpha-7 receptor agonist compound (R)-7-chloro-N-(quinuclidin-3-yl)benzo[b]thiophene-2-carboxamide hydrochloride was disclosed in United States Patent Application Publication No. US 2005-0119325. However, in contrast to the present invention, such disclosure did not disclose or suggest the present invention, (R)-7-chloro-N-(quinuclidin-3-yl)benzo[b]thiophene-2-carboxamide hydrochloride monohydrate, nor did it disclose any crystal forms of (R)-7-chloro-N-(quinuclidin-3-yl)benzo[b]thiophene-2-carboxamide hydrochloride monohydrate.

In one embodiment, the invention provides a crystalline Form I of (R)-7-chloro-N-(quinuclidin-3-yl)benzo[b]thiophene-2-carboxamide hydrochloride monohydrate, characterized by an x-ray powder diffraction pattern having peaks expressed as 2θ at one or both of 17.48 and 20.58±0.20 degrees when measured against an internal silicon standard.

In another embodiment, the invention provides the crystalline Form I as defined above, characterized by an x-ray powder diffraction pattern further having at least one peak expressed as 2θ at 4.50, 9.04, 14.60, 15.14, 15.80, 16.60, 18.16, 18.44, 19.48, 21.74, and 25.46±0.20 degrees when measured against an internal silicon standard.

In another embodiment, the invention includes the crystalline Form I as defined above, characterized by an x-ray powder diffraction pattern further having at least two peaks expressed as 2θ at 4.50, 9.04, 14.60, 15.14, 15.80, 16.60, 18.16, 18.44, 19.48, 21.74 and 25.46±0.20 degrees when measured against an internal silicon standard.

In yet another embodiment, the invention provides the crystalline Form I as defined above, characterized by an x-ray powder diffraction pattern further having at least four peaks expressed as 2θ at 4.50, 9.04, 14.60, 15.14, 15.80, 16.60, 18.16, 18.44, 19.48, 21.74 and 25.46±0.20 degrees when measured against an internal silicon standard.

The invention further includes the crystalline Form I as defined above, characterized by an x-ray powder diffraction pattern further having at least six peaks expressed as 2θ at 4.50, 9.04, 14.60, 15.14, 15.80, 16.60, 18.16, 18.44, 19.48, 21.74 and 25.46±0.20 degrees when measured against an internal silicon standard.

The invention further includes the crystalline Form I as defined above, characterized by an x-ray powder diffraction pattern further having at least eight peaks expressed as 2θ at 4.50, 9.04, 14.60, 15.14, 15.80, 16.60, 18.16, 18.44, 19.48, 21.74 and 25.46±0.20 degrees when measured against an internal silicon standard.

The invention further provides the crystalline Form I as defined above, characterized by an x-ray powder diffraction pattern further having peaks expressed as 2θ at 4.50, 9.04, 14.60, 15.14, 15.80, 16.60, 18.16, 18.44, 19.48, 21.74 and 25.46±0.20 degrees when measured against an internal silicon standard.

In another embodiment, the present invention provides a crystalline Form II of (R)-7-chloro-N-(quinuclidin-3-yl)benzo[b]thiophene-2-carboxamide hydrochloride monohydrate, characterized by an x-ray powder diffraction pattern having peaks expressed as 2θ at one or both of 21.16 and 21.38±0.20 degrees when measured against an internal silicon standard.

In another embodiment, the present invention provides the crystalline Form II as defined above, characterized by an x-ray powder diffraction pattern further having at least one peak expressed as 2θ at 4.48, 9.00, 13.58, 15.62, 16.48, 19.02, 19.44, 22.46 and 25.00±0.20 degrees when measured against an internal silicon standard.

In yet another embodiment, provided herein is the crystalline Form II as defined above, characterized by an x-ray powder diffraction pattern further having at least two peaks expressed as 2θ at 4.48, 9.00, 13.58, 15.62, 16.48, 19.02, 19.44, 22.46 and 25.00±0.2 degrees when measured against an internal silicon standard.

In another embodiment, the present invention includes the crystalline Form II as defined above, characterized by an x-ray powder diffraction pattern further having at least four peaks expressed as 2θ at 4.48, 9.00, 13.58, 15.62, 16.48, 19.02, 19.44, 22.46 and 25.00±0.2 degrees when measured against an internal silicon standard.

Further provided herein is the crystalline Form II as defined above, characterized by an x-ray powder diffraction pattern further having at least six peaks expressed as 2θ at 4.48, 9.00, 13.58, 15.62, 16.48, 19.02, 19.44, 22.46 and 25.00±0.2 degrees when measured against an internal silicon standard.

Also provided here is the crystalline Form II as defined above, characterized by an x-ray powder diffraction pattern further having at least eight peaks expressed as 2θ at 4.48, 9.00, 13.58, 15.62, 16.48, 19.02, 19.44, 22.46 and 25.00±0.2 degrees when measured against an internal silicon standard.

In another embodiment, provided herein is the crystalline Form II as defined above, characterized by an x-ray powder diffraction pattern further having peaks expressed as 2θ at 4.48, 9.00, 13.58, 15.62, 16.48, 19.02, 19.44, 22.46 and 25.00±0.2 degrees when measured against an internal silicon standard.

III. Methods of the Invention

A. Methods of Use

In an embodiment, the present invention provides the crystalline Form I for the treatment and/or prophylaxis of a disease which can be treated or prevented by alpha-7 receptor activation. In another embodiment, the present invention provides crystalline Form II for the treatment and/or prophylaxis of a disease which can be treated or prevented by alpha-7 receptor activation.

In another embodiment, the present invention provides a method of treating or preventing a disease which can be treated or prevented by alpha-7 receptor activation comprising administering to a subject crystalline Form I. In another embodiment, a method of treating or preventing a disease which can be treated or prevented by alpha-7 receptor activation comprising administering to a subject crystalline Form II is provided.

In another embodiment, the present invention provides a method for improving cognition or treating cognitive loss in a subject comprising administering to a subject the crystalline Form I. In another embodiment, the present invention provides the method for improving cognition or treating cognitive loss by administering to a subject the crystalline Form I wherein the subject is suffering from a disorder selected from: attention deficit disorder, attention deficit hyperactivity disorder, and Parkinson's Disease. In another embodiment, the present invention provides the method for improving cognition or treating cognitive loss by administering crystalline Form I wherein the subject is suffering from a disorder selected from Alzheimer's Disease and schizophrenia.

In another embodiment, the present invention provides a method of treating a disorder selected from attention deficit disorder, attention deficit hyperactivity disorder, Parkinson's Disease, Alzheimer's Disease and schizophrenia, the method comprising administering to a subject the crystalline Form I. In another embodiment, the present invention includes a method of treating a subject that is at risk for developing a disorder selected from: Alzheimer's disease, Parkinson's Disease and schizophrenia, the method comprising administering to the subject the crystalline Form I. In yet another embodiment, the present invention includes a method of treating a subject over age 60, comprising administering to the subject the crystalline Form I. In a further embodiment, the present invention includes a method of treating a subject for age-related memory loss, comprising administering to the subject the crystalline Form I. In another embodiment the present invention includes a method of treating a subject for age-related memory loss, comprising administering to the subject the crystalline Form I wherein the subject is over age 60.

In another embodiment, the present invention provides a method for improving cognition or treating cognitive loss in a subject comprising administering to a subject the crystalline Form II. In another embodiment, the present invention provides the method for improving cognition or treating cognitive loss by administering crystalline Form II to a subject, wherein the subject is suffering from a disorder selected from: attention deficit disorder, attention deficit hyperactivity disorder, and Parkinson's Disease. In another embodiment, the present invention provides the method for improving cognition or treating cognitive loss by administering crystalline Form II to a subject, wherein the subject is suffering from a disorder selected from Alzheimer's Disease and schizophrenia.

In another embodiment, the present invention provides a method of treating a disorder selected from attention deficit disorder, attention deficit hyperactivity disorder, Parkinson's Disease, Alzheimer's Disease and schizophrenia, the method comprising administering to a subject the crystalline Form II. In another embodiment, the present invention includes a method of treating a subject that is at risk for developing a disorder selected from: Alzheimer's disease, Parkinson's Disease and schizophrenia, the method comprising administering to the subject the crystalline Form II. In yet another embodiment, the present invention includes a method of treating a subject over age 60, comprising administering to the subject the crystalline Form II. In a further embodiment, the present invention includes a method of treating a subject for age-related memory loss, comprising administering to the subject the crystalline Form II. In another embodiment the present invention includes a method of treating a subject for age-related memory loss, comprising administering to the subject the crystalline Form II wherein the subject is over age 60.

B. Methods of Preparation

It would be beneficial to provide (R)-7-chloro-N-(quinuclidin-3-yl)benzo[b]thiophene-2-carboxamide hydrochloride monohydrate in a stable crystalline form. After extensive studies, two types of stable crystalline forms were identified: Form I and Form II. One crystalline form does not convert to the other readily in solid condition because each of two crystalline forms is stable. On the other hand, it was found that when one crystalline form was dissolved in an aqueous solvent and the crystallization was carried out from the solution, it was difficult to predict which crystalline form was preferentially produced. In addition, one form might be converted to the other or a mixture of two forms quite easily in the solution under certain conditions. Therefore the mechanism of crystallization was unclear, and it was difficult to design methods for producing each form at high purity. After extensive investigation, the inventors arrived at the methods for selectively manufacturing each pure crystalline form. The methods can be carried out using a variety of different solvents.

A crystal form of a compound is usually obtained by: 1) dissolving the compound in a solvent at a high temperature, where the solubility of the product is high, 2) lowering the temperature of the solution to cause crystallization of the compound, and 3) isolating the resulting crystals.

However, solid state investigations revealed that there are two enantiotropic crystalline forms of (R)-7-chloro-N-(quinuclidin-3-yl)benzo[b]thiophene-2-carboxamide hydrochloride monohydrate, and the present inventors discovered that the usual crystallization procedure is apt to produce a mixture of the two crystal forms of the compound. This is because at higher temperatures, one crystal form of the compound is a little more stable in a solvent system, whereas in at lower temperatures, the other crystal form of the compound is a little more stable in the same solvent system. This effect can be seen in Examples 5, 6, 7 and 8. Furthermore, the boundary temperature for converting from one form to the other was found to vary depending on the solvent system in which the compound is dissolved.

The inventors extensively investigated the stable crystal forms at various temperatures and in various solvent systems and recognized that Form I and Form II of (R)-7-chloro-N-(quinuclidin-3-yl)benzo[b]thiophene-2-carboxamide hydrochloride monohydrate can be separately prepared based on the relationship of temperature and water activity of the solvent independently of the particular organic solvent. This recognition led to the creation of novel methods for separately manufacturing pure Form I and pure Form II.

In an embodiment, the present invention provides a method for preparing a pharmaceutical composition, the method comprising combining the crystalline form I with an excipient or pharmaceutically acceptable carrier. In an embodiment, the method further includes combining the crystalline form I with a liquid. In a further embodiment, the method includes filling a capsule with a composition comprising the crystalline form I.

In another embodiment, the present invention includes a method for preparing a pharmaceutical composition comprising combining the crystalline form II with an excipient or pharmaceutically acceptable carrier. In an embodiment, the method further includes combining the crystalline form II with a liquid. In a further embodiment, the method includes filling a capsule with a composition comprising the crystalline form II.

A method of manufacturing a crystalline Form I comprises: (1) stirring (R)-7-chloro-N-(quinuclidin-3-yl)benzo[b]thiophene-2-carboxamide hydrochloride (hereinafter, "(R)-7-chloro-N-(quinuclidin-3-yl)benzo[b]thiophene-2-carboxamide hydrochloride" includes any form of anhydrate, hydrate and solvate, preferably anhydrate and hydrate) in an aqueous organic solvent within the temperature-water activity range I, if required with decreasing the temperature and/or water activity thereof, to form a substantially pure crystalline Form I; and (2) isolating the resulting crystalline Form I, wherein the temperature-water activity range I is defined by the following relationship of the temperature and the water activity of the aqueous organic solvent, the water activity (x) of the aqueous organic solvent is from 0.16 to 0.73; and the temperature (T) of the aqueous organic solvent is higher than (183x−64.2) and lower than the boiling temperature of the aqueous organic solvent.

In an embodiment, the method of manufacturing crystalline Form I includes a method where, in step (1) the initial state of (R)-7-chloro-N-(quinuclidin-3-yl)benzo[b]thiophene-2-carboxamide hydrochloride in an aqueous organic solvent is a solution, and the solution is stirred within the temperature-water activity range I with decreasing the temperature and/or water activity thereof. In another embodiment, the method of manufacturing crystalline Form I includes a method where in step (1) the initial state of (R)-7-chloro-N-(quinuclidin-3-yl)benzo[b]thiophene-2-carboxamide hydrochloride in an aqueous organic solvent is a suspension, and the suspension is stirred within the temperature-water activity range I, if required with decreasing the temperature and/or water activity thereof. In a further embodiment, the method of manufacturing crystalline Form I includes a method where in step (1) the seed crystals of (R)-7-chloro-N-(quinuclidin-3-yl)benzo[b]thiophene-2-carboxamide hydrochloride is added to the solution. In a still further embodiment, the method of manufacturing crystalline Form I includes a method where the seed crystals are Form I of (R)-7-chloro-N-(quinuclidin-3-yl)benzo[b]thiophene-2-carboxamide hydrochloride monohydrate.

In an embodiment the method of manufacturing crystalline Form I includes a method where the water activity is from 0.29 to 0.59. In another embodiment, the method of manufacturing crystalline Form I includes a method where the temperature is between −10° C. and 60° C. and higher than the following T: T=183x−57.6; wherein x is water activity of the aqueous organic solvent and T is a temperature (° C.). In yet another embodiment the method of manufacturing crystalline Form I includes a method where the end point temperature in step (1) is between 0° C. and 35° C.

In an embodiment, the method of manufacturing crystalline Form I includes a method where the aqueous organic solvent is mixture of water and one or more of organic solvents which are miscible with water and are selected from alcohols, ketones, nitriles and ethers. In another embodiment, the method of manufacturing crystalline Form I includes a method where the aqueous organic solvent is mixture of water and one or more of organic solvents which are miscible with water and are selected from propanol, butanol, butanone and acetonitrile.

The present invention also includes a method of manufacturing a crystalline Form II; comprising: (1) stirring (R)-7-chloro-N-(quinuclidin-3-yl)benzo[b]thiophene-2-carboxamide hydrochloride in an aqueous organic solvent within the temperature-water activity range II, if required with decreasing the temperature and/or water activity thereof, to form a crystalline Form II, and (2) isolating the resulting crystalline Form II, wherein the temperature-water activity range II is defined by the following relationship of the temperature and the water activity of the aqueous organic solvent, the water activity (x) of the aqueous organic solvent is from 0.16 to 0.73; and the temperature (T) of the aqueous organic solvent is lower than (183x−64.2) and higher than the freezing-point temperature of the aqueous organic solvent.

In an embodiment, the method of manufacturing crystalline Form II includes the method where in step (1) the initial state of (R)-7-chloro-N-(quinuclidin-3-yl)benzo[b]thiophene-2-carboxamide hydrochloride in an aqueous organic solvent is a solution, and the solution is stirred within the temperature-water activity range II with decreasing the temperature and/or water activity thereof. In an embodiment, the method of manufacturing crystalline Form II includes a method wherein in step (1) the initial state of (R)-7-chloro-N-(quinuclidin-3-yl)benzo[b]thiophene-2-carboxamide hydrochloride in an aqueous organic solvent is a suspension, and the suspension is stirred within the temperature-water activity range II, optionally decreasing the temperature and/or water activity thereof.

In another embodiment, the method of manufacturing crystalline Form II includes a method wherein in step (1) the seed crystals of (R)-7-chloro-N-(quinuclidin-3-yl)benzo[b]thiophene-2-carboxamide hydrochloride is added to the solution. In yet another embodiment, the method of manufacturing crystalline Form II includes a method wherein the seed crystals are Form II of (R)-7-chloro-N-(quinuclidin-3-yl)benzo[b]thiophene-2-carboxamide hydrochloride monohydrate. In yet another embodiment, the method of manufacturing crystalline Form II includes a method wherein the water activity is from 0.29 to 0.59. In a further embodiment, the method of manufacturing crystalline Form II includes a method wherein the temperature is between −10° C. and 60° C. and lower than the following T: T=183x−70.8; wherein x is water activity of the aqueous organic solvent and T is a temperature (° C.). In an embodiment, the method of manufacturing crystalline Form II includes a method wherein the end point temperature in step (1) is between 0° C. and 35° C. In an embodiment, the method of manufacturing crystalline Form II includes a method wherein the aqueous organic solvent is mixture of water and one or more of organic solvents which are miscible with water and are selected from alcohols, ketones, nitriles and ethers.

In another embodiment, the method of manufacturing crystalline Form II includes a method wherein the aqueous organic solvent is mixture of water and one or more of organic solvents which are miscible with water and are selected from propanol, butanol, butanone and acetonitrile.

The present invention also provides another method for preparing the crystalline Form I, comprising: (a) heating 10-30% by weight of (R)-7-chloro-N-(quinuclidin-3-yl)benzo[b]thiophene-2-carboxamide hydrochloride in acetonitrile or an aqueous acetonitrile to between 60° C. and the boiling point of the solution, (b) optionally adding water to the mixture to fully dissolve the (R)-7-chloro-N-(quinuclidin-3-yl)benzo[b]thiophene-2-carboxamide hydrochloride; (c) cooling the solution until crystals are just visible; (d) if the water content is greater than 3% volume/volume when crystals are just visible, adding acetonitrile to the mixture so that the water content is less than 3% volume/volume; (e) cooling the resulting mixture to below 15° C.; and (f) isolating crystalline (R)-7-chloro-N-(quinuclidin-3-yl)benzo[b]thiophene-2-carboxamide hydrochloride monohydrate.

In an embodiment, the method of preparing the crystalline Form I includes the method as defined in steps (a) through (f) above, wherein the water added in step (a) does not bring the water content of the mixture above 30% volume/volume. In another embodiment, the method of preparing the crystalline Form I includes the method as defined in steps (a) through (f) above, wherein (R)-7-chloro-N-(quinuclidin-3-yl)benzo[b]thiophene-2-carboxamide hydrochloride is present at 15-25% by weight in step (a). In another embodiment, the method of preparing the crystalline Form I includes the method as defined in steps (a) through (f) above, wherein (R)-7-chloro-N-(quinuclidin-3-yl)benzo[b]thiophene-2-carboxamide hydrochloride is present at 16-20% by weight in step (a). In another embodiment, the method of preparing the crystalline Form I includes the method as defined in steps (a) through (f) above, wherein (R)-7-chloro-N-(quinuclidin-3-yl)benzo[b]thiophene-2-carboxamide hydrochloride is present at 17-19% by weight in step (a). In yet another embodiment, the method of preparing the crystalline Form I includes the method as defined in steps (a) through (f) above, further comprising adding Form I (R)-7-chloro-N-(quinuclidin-3-yl)benzo[b]thiophene-2-carboxamide hydrochloride monohydrate to the mixture after crystals are just visible.

In yet another embodiment, the method of preparing the crystalline Form I includes the method as defined in steps (a) through (f) above, wherein step (c) comprises cooling the solution to below 55° C. In yet another embodiment, the method of preparing the crystalline Form I includes the method as defined in steps (a) through (f) above, wherein step (c) comprises cooling the solution to below 50° C.

Also included in the present invention is a method for preparing the crystalline Form II, the method comprising: (a) heating 5-15% by weight of (R)-7-chloro-N-(quinuclidin-3-yl)benzo[b]thiophene-2-carboxamide hydrochloride in 2-butanol or an aqueous 2-butanol to between 60° C. and the boiling point of the solution; (b) if the water content is smaller than 5% volume/volume, adding water to the mixture so that the water content is not less than 5% volume/volume; (c) cooling the solution to below 10° C.; (d) keeping the resulting mixture to below 10° C.; and (e) isolating crystalline (R)-7-chloro-N-(quinuclidin-3-yl)benzo[b]thiophene-2-carboxamide hydrochloride monohydrate.

The present invention further includes a method for preparing the crystalline Form II, the method comprising: (a) adding (R)-7-chloro-N-(quinuclidin-3-yl)benzo[b]thiophene-2-carboxamide hydrochloride to (i) acetonitrile or (ii) aqueous acetonitrile to create a composition that is 10-20% by weight of (R)-7-chloro-N-(quinuclidin-3-yl)benzo[b]thiophene-2-carboxamide hydrochloride; (b)

optionally adding water to the composition to make the water content 6-10%; (c) optionally cooling the solution at below 10° C.; (d) allowing crystals to form; and (e) isolating crystalline (R)-7-chloro-N-(quinuclidin-3-yl)benzo[b]thiophene-2-carboxamide hydrochloride monohydrate.

The crystalline Forms I and II are very stable in many aspects. Both forms are stable under storage conditions. No degradation products from either form were detected under the storage conditions: 11% RH at 40° C., 75% RH at 40° C., 11% RH at 60° C. and 75% RH at 60° C. after 2 weeks, and no degradation products from either form were detected under the photo storage conditions: exposure to light (D65 lamp) of 1.2 million Lux hours at 25° C. Both forms are also stable under physical stress. The XRD charts of both forms were not changed after compression experiments with a planar pestle (1000 kgf/cm$^2$).

The pure crystalline Forms I and II can be manufactured by the special methods, which are described herein.

Figure 4:
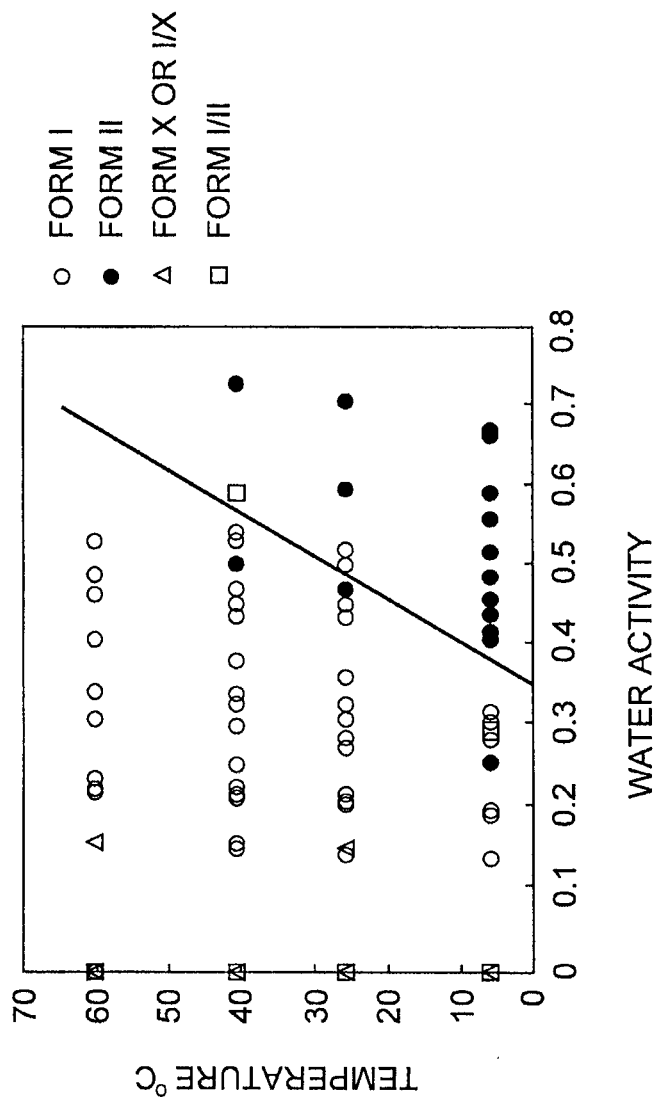
FIG. 4 depicts a diagram of Form I and Form II using plots of temperature against the value of water activity.

Pure crystalline Form I can be manufactured by a method which comprises: (1) stirring (R)-7-chloro-N-(quinuclidin-3-yl)benzo[b]thiophene-2-carboxamide hydrochloride in an aqueous organic solvent within the temperature-water activity range I (as depicted in FIG. 4), if required with decreasing the temperature and/or water activity thereof, to form a substantially pure crystalline Form I, and (2) isolating the resulting crystalline Form I.

Pure crystalline Form II can be manufactured by the method which comprises: (1) stirring (R)-7-chloro-N-(quinuclidin-3-yl)benzo[b]thiophene-2-carboxamide hydrochloride in an aqueous organic solvent within the temperature-water activity range II (as depicted in FIG. 4), if required with decreasing the temperature and/or water activity thereof, to form a crystalline Form II, and (2) isolating the resulting crystalline Form II.

Water activity is a thermophysical coefficient used to represent the energy status of the water in a system and is defined as the vapor pressure of water above a sample divided by that of pure water at the same temperature. It can be measured with a capacitance hygrometer or a dew point hygrometer. It can be also predicted by COSMO-RS method (Fluid Phase Equililbria, 172 (2000) 43-72).

(R)-7-chloro-N-(quinuclidin-3-yl)benzo[b]thiophene-2-carboxamide hydrochloride was prepared, for example, by the method described in WO03/55878. 7-Chloro-benzo[b]thiophene-2-carboxylic acid was reacted with carbonyldiimidazole to give 7-chloro-2-imidazolyl-carbonylbenzo[b]thiophene, followed by reacting with (R)-3-aminoquinuclidine dihydrochloride to give (R)-7-chloro-N-(quinuclidin-3yl)benzo[b]thiophene-2-carboxamide hydrochloride.

(R)-7-chloro-N-(quinuclidin-3-yl)benzo[b]thiophene-2-carboxamide hydrochloride used for the above manufacturing methods can be for example crystals (e.g., Forms I, II, and mixtures thereof), amorphous products, an oil or a solution, and preferably a solution. The crystallization can be performed in the same vessel after hydrochlorination. An aqueous organic solvent is a mixture of water and one or more organic solvents. The preferable organic solvents are water-miscible organic solvents, and more preferable are for example alcohols (e.g., $C_{1-6}$alkanol such as methanol, ethanol, 1-propanol, 2-propanol, 1-butanol, 2-butanol, and $C_{2-6}$alkanediol such as ethylene glycol, propylene glycol), ketones (e.g., $C_{3-6}$alkanone such as acetone, butanone), nitriles (e.g., acetonitrile, propanonitrile) and ethers (e.g. dimethoxyethane, tetrahydrofuran). Preferable solvents are alcohols, nitriles and ketones, and more preferable are propanols, butanols, butanone and acetonitrile.

In the present invention the solution is supersaturated prior to the formation of crystals. The boundary between the temperature-water activity ranges for Forms I and II is shown in FIG. 4 as a line which divides the domains of Forms I and II.

Crystal forms may be monitored during the production method. Any analytical methods can be used for monitoring as long as it can distinguish crystal forms, and XRD is one of most preferable methods. In order to manufacture a pure form, stirring of the mixture is continued until undesired form completely converts to the desired form.

In the method for manufacturing Form I, Form X which is different from both Forms I and II may appear temporally, but Form X can be converted to Form I and disappears if stirring of the mixture is continued.

IV. Pharmaceutical Compositions of the Invention

Provided also herein the present invention is a pharmaceutical composition comprising the crystalline Form I. Also provided herein is a pharmaceutical composition comprising the crystalline Form II.

The crystalline Forms I and II may be used to prepare a medicament to treat disease or condition in a mammal in need thereof, wherein mammal would receive symptomatic relief from the administration of a therapeutically effective amount of a crystalline Form I or II. The crystalline Forms I and II may be administered in combination with other medications for additive or synergistic therapeutic benefit for a given disease. Diseases include, but are not limited to, those described below. Medications include, but are not limited to, drugs which are approved for a given indication e.g. acetylcholinesterase inhibitors for Alzheimer's Disease.

Because Form I is very stable and can be stored for a considerable length of time prior to its use in the preparation of a drug product, Form I is useful in the manufacture of drug product even when the manufacturing process, i.e., the formulation of the active ingredient, causes some or all of the Form I to convert to another form.

The crystalline Forms I and II may be formulated as solutions or suspensions, in the form of tablets, capsules (each including timed release and sustained release formulations), pills, oils, powders, granules, elixirs, tinctures, suspensions, syrups, emulsions, microemulsions, or with excipients. Likewise, they may also be administered by any conventional route, for example in intravenous (both bolus and infusion), intraperitoneal, intraocularly, subcutaneous, intramuscular form, enterally, preferably orally (e.g., in the form of tablets or capsules), or in a nasal, buccal, sub-lingual, transdermal, or a suppository form, using well known formulations to those of ordinary skill in the pharmaceutical arts. In addition, the crystalline Forms I and II can be administered in the form of liposomes or the like. Disintegrators include, without limitation, delivery systems such as small unilamellar vesicles, large unilamellar vesicles and multilamellar vesicles. Liposomes can be formed from a variety of phospholipids, such as cholesterol, stearylamine or phosphatidylcholines.

For oral administration in the form of a tablet or capsule, the crystalline Forms I and II can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Suitable lubricants used in these dosage forms include, for example, sodium oleate, sodium stearate, magnesium stearate, sodium benzoate, sodium acetate, sodium chloride and the like. Suitable disintegrating agents are, for example, starches, carboxymethylstarch sodium, crosscarmellose sodium and the like. Examples of the suitable coloring agents are iron sesquioxide, yellow iron sesquioxide, amaranth, erythrosine, tartrazine, Sunset Yellow FCF and the like.

The dosage regimen for the crystalline Forms I and II is selected in accordance with a variety of factors including type, species, age, weight, sex and medical condition of the patient; the severity of the condition to be treated; the route of administration; the renal and hepatic function of the patient. An ordinarily skilled physician or veterinarian can readily determine and prescribe the effective amount of the drug required to prevent, counter or arrest the progress of the condition.

In one embodiment satisfactory results in animals are indicated to be obtained at a daily dosage of from about 0.1 to about 600 mg or from about 0.01 to about 5 mg/kg animal body weight.

Injected intravenous, subcutaneous or intramuscular dosages of the crystalline Forms I and II, when used for the indicated effects, will range between about 0.001 to 1.0 mg/kg. Furthermore, the crystalline Forms I and II can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Transdermal delivery can also be achieved using approaches known to those skilled in the art.

Diseases that may be treated using the crystalline Forms I and II include, but are not limited to: condition cognitive and attention deficit symptoms of Alzheimer's, neurodegeneration associated with diseases such as Alzheimer's disease, pre-senile dementia (mild cognitive impairment), senile dementia, schizophrenia, psychosis attention deficit disorder, attention deficit hyperactivity disorder, mood and affective disorders, amytrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntingdon disease, depression, general anxiety disorder, age related macular degeneration, Parkinson's disease, tardive dyskinesia, Pick's disease, post traumatic stress disorder, dysregulation of food intake including bulimia and anorexia nervosa, withdrawal symptoms associated with smoking cessation and dependant drug cessation, Gilles de la Tourette's Syndrome, glaucoma, neurodegeneration associated with glaucoma or symptoms associated with pain or is the treatment and/or prophylaxis for the improvement of perception, concentration, learning and/or memory.

EXEMPLIFICATION

The present invention is illustrated by the following examples, which are not intended to be limiting in any way.

Example 1

Preparation of the Crystalline Form I (R)-7-Chloro-N-(quinuclidin-3-yl)benzo[b]thiophene-2-carboxamide hydrochloride was synthesized by the procedure described in US 2005-0119325. To prepare Form I, 1.0 Kg of the compound was dissolved in acetonitrile (5 L) and heated to 72-78° C. Once at this temperature, water (0.5 L) was added. The mixture was cooled to 50-60° C., wherein crystals are just visible and seed with Form I seed crystals. The mixture was held for a minimum of 2 hours, and then acetonitrile (20 L) was added while maintaining an internal temperature of 50-60° C. The material was cooled to 5-10° C. Crystals were isolated by vacuum filtration and washed with acetonitrile (2 L). The material was dried at 40° C. in a vacuum oven with humidity control to provide 0.8 kg of pure Form I.

Example 2

Preparation of the Crystalline Form I

Acetonitrile (90 mL) and water (10 mL) were mixed at room temperature. 1.0 ml of this solution was added to 100.7 mg of the crystalline Form I of (R)-7-chloro-N-(quinuclidin-3-yl)benzo[b]thiophene-2-carboxamide hydrochloride monohydrate. This suspension was stirred at 80° C. until solid component was dissolved, then the temperature was decreased to 40° C. for 80 minutes. During the cooling, spontaneous crystallization was observed round 52° C. To the suspension, 2.40 ml of acetonitrile was dropped slowly, and then the temperature was decreased to 10° C. for 60 minutes. The suspension was stirred at same temperature for 15 hours, and then the solid was filtered and washed with 0.20 ml of acetonitrile. After vacuum drying, 81.1 mg of the crystalline Form I was recovered.

Example 3

Preparation of the Crystalline Form II

Acetonitrile (90 mL) and water (10 mL) were mixed at room temperature. 1.0 ml of this solution was added to 100.9 mg of the crystalline Form I of (R)-7-chloro-N-(quinuclidin-3-yl)benzo[b]thiophene-2-carboxamide hydrochloride monohydrate. This suspension was stirred at 80° C. until solid component was dissolved, then the temperature was decreased to 10° C. for 140 minutes. During the cooling, spontaneous crystallization was observed round 51° C. The suspension was stirred at same temperature for 15 hours, then the solid was filtered and washed with 0.20 ml of acetonitrile. After vacuum drying, 48.7 mg of the crystalline Form II was recovered.

Example 4

Preparation of the Crystalline Form II (R)-7-chloro-N-(quinuclidin-3-yl)benzo[b]thiophene-2-carboxamide hydrochloride monohydrate (462 g) was triturated in 2308.5 mL acetonitrile and 230.85 mL of water at ambient temperature for 4.75 hours. The producted was isolated by filtration and dried to afford 314 g of isolated pure Form II.

Example 5

Phase Diagram in Aqueous Acetonitrile (1) Solubility Measurements of Forms I and II
Solubility of Forms I and II was measured at various temperatures between 5° C. and 45° C. in aqueous acetonitrile in which water concentration was from 0 to 10 v/v % respectively.

Solubility was measured according to the following procedure. Form I or II crystals and an aqueous acetonitrile were added to a glass vessel. The mixture was stirred with a Teflon-coated magnetic stirrer bar at a defined temperature controlled with aluminum block. The liquid phase was sampled periodically, and the concentration of the compound was measured with high performance liquid chromatography (HPLC). Solid material was also collected at the same time to identify the crystal form using XRPD. In analyzing the time course of the change in concentration, that plateau zone was identified as an equilibrium condition, and the mean value of these concentrations was defined as "solubility" under that condition. Measured solubility is summarized in Table 1.

TABLE 1

Results of the solubility measurement

| Conditions | | | | | Stable form |
|---|---|---|---|---|---|
| Water concentration | Temp | Solubility | | | (Estimated from |
| [v/v %] | [° C.] | Form I | Form II | Form X | solubility) |
| 0 | 5 | 1.0 | * | ** | I |
|  | 25 | 1.3 | * | ** | I |
| 2 | 5 | 2.4 | 2.6 | ** | I |
|  | 25 | 4.1 | 4.7 | 4.2 | I |
|  | 45 | 8.7 | * | 9.1 | I |
| 3.5 | 12.5 | 5.4 | 5.7 | ** | I |
|  | 37.5 | 10.0 | * | 10.3 | I |
| 6 | 5 | 12.8 | 11.2 | ** | II |
|  | 25 | 17.1 | 16.7 | ** | II |
|  | 45 | 27.2 | 29.6 | ** | I |
| 8.5 | 12.5 | 27.6 | 25.1 | ** | II |
|  | 37.5 | 44.4 | 44.4 | ** | I and II |
| 10 | 5 | * | 29.7 | ** | II |
|  | 25 | 47.5 | 44.6 | ** | II |
|  | 45 | 71.6 | 74.5 | ** | I |

* Could not measure
** Did not conduct (2) Solubility Equations were Modeled Using JMP 6 (SAS Institute)

With the response surface method, measured solubility values were applied to equation (1) to obtain solubility models as a function of temperature and water concentration. W' and T' were defined as equations (2) and (3) respectively. Here, $C^*_x$, W and T mean solubility of a certain crystal form, water concentration in aqueous acetonitrile (v/v %) and temperature (° C.) respectively. Constant values from a, b, c, d and f were determined by applying measured solubility values with least squares fitting method within the range of 2 to 10 v/v % water concentration and within the range of 5 to 45° C. Perspective of defects or accuracy, measured solubility values at 2%-45° C. of both forms, 3.5%-37.5° C. of form II and 10%-10.0° C. of form I are excluded to build mathematical formulas.

$$C^*_x = \text{Exp}(a+bW'+cT'+dW'T'+eW'^2+fT'^2) \quad (1)$$

$$W'=(W-6)/4 \quad (2)$$

$$T'=(T-25)/20 \quad (3)$$

Fitting results showed that constants were determined successfully, and these models can describe solubility within the range with only minor deviation. Obtained solubility equations of Forms I and II are shown in equation (4) and (5) respectively.

$$C^*_I = \text{Exp}(2.8448+1.2517W'+0.4185T'-0.1086W'T'-0.2249W'^2+0.0681T'^2) \quad (4)$$

$$C^*_{II} = \text{Exp}(2.8389+1.1503W'+0.5101T'-0.0638W'T'-0.1888W'^2+0.0488T'^2) \quad (5)$$

(3) Development of Phase Diagram

Thermodynamic relationship between polymorphic crystal phases is consistent with solubility. Based on the results of the solubility measurements, it is apparent that thermodynamic relationship between forms I and II crystals is enantiotropy. Boundary of stable crystal form should exist in the range that solubility measurement was carried out. At boundary condition, solubility of forms I and II should be same. Hence, boundary condition can be induced from equation (4) and (5) and simplified as described in equation (6).

$$0.0059+0.1014W'-0.0916T'-0.0448W'T'-0.0361W'^2+0.0193T'^2=0 \quad (6)$$

By solving boundary equation (6), boundary condition can be determined. Solved values are shown in Table 2. By plotting the results, phase diagram was described in FIG. 1. For convenience, this boundary line which obtained from equation (6) was fitted by fourth degree equation of water concentration. This approximation formula and its solved values are shown in equation (7) and Table 2 respectively.

$$T=0.0056W^4-0.1305W^3+0.2831W^2+11.3942W-31.3235 \quad (7)$$

TABLE 2

Solved values of boundary equations

| Water concentration | Temperature[° C.] | |
|---|---|---|
| [% v/v] | Equation (6) | Equation (7) |
| 3.0 | 2.34 | 2.34 |
| 3.5 | 7.26 | 7.27 |
| 4.0 | 11.86 | 11.86 |
| 4.5 | 16.08 | 16.09 |
| 5.0 | 19.91 | 19.91 |
| 5.5 | 23.33 | 23.32 |
| 6.0 | 26.31 | 26.30 |
| 6.5 | 28.85 | 28.86 |
| 7.0 | 30.97 | 30.99 |
| 7.5 | 32.69 | 32.72 |
| 8.0 | 34.03 | 34.07 |
| 8.5 | 35.03 | 35.07 |
| 9.0 | 35.73 | 35.76 |
| 9.5 | 36.16 | 36.20 |
| 10.0 | 36.35 | 36.43 |

Example 6

Inter-Conversion Tests

Inter-conversion tests were also carried out in order to confirm reliability of obtained phase diagram of Example 5 (FIG. 1).

Solvent was added to a glass vessel and temperature was controlled with aluminum block. Identical amounts of Forms I and II crystals were added to the vessel. The solutions were stirred for 13 to 40 hr with Teflon-coated magnetic stirrer bar. Solid component was sampled and analyzed with XRPD to determine its crystal form.

The results were summarized in Table 3. These results were consistent with phase diagram of Example 5.

TABLE 3

Experimental Results of Inter-conversion tests

| run | Temperature [° C.] | Water concentration [v/v %] | Results |
|---|---|---|---|
| 1 | 10 | 3.0 | I |
| 2 | | 3.5 | I |
| 3 | | 4.0 | II |
| 4 | | 4.5 | II |
| 5 | 20 | 4.0 | I |
| 6 | | 4.5 | I |
| 7 | | 5.0 | I |
| 8 | | 5.5 | II |
| 9 | | 6.0 | II |
| 10 | 30 | 5.5 | I |
| 11 | | 6.0 | I |
| 12 | | 6.5 | I |
| 13 | | 7.0 | I |
| 14 | | 7.5 | II |

Example 7

Crystallization Behavior in Aqueous Acetonitrile (1) Form X

Figure 2:
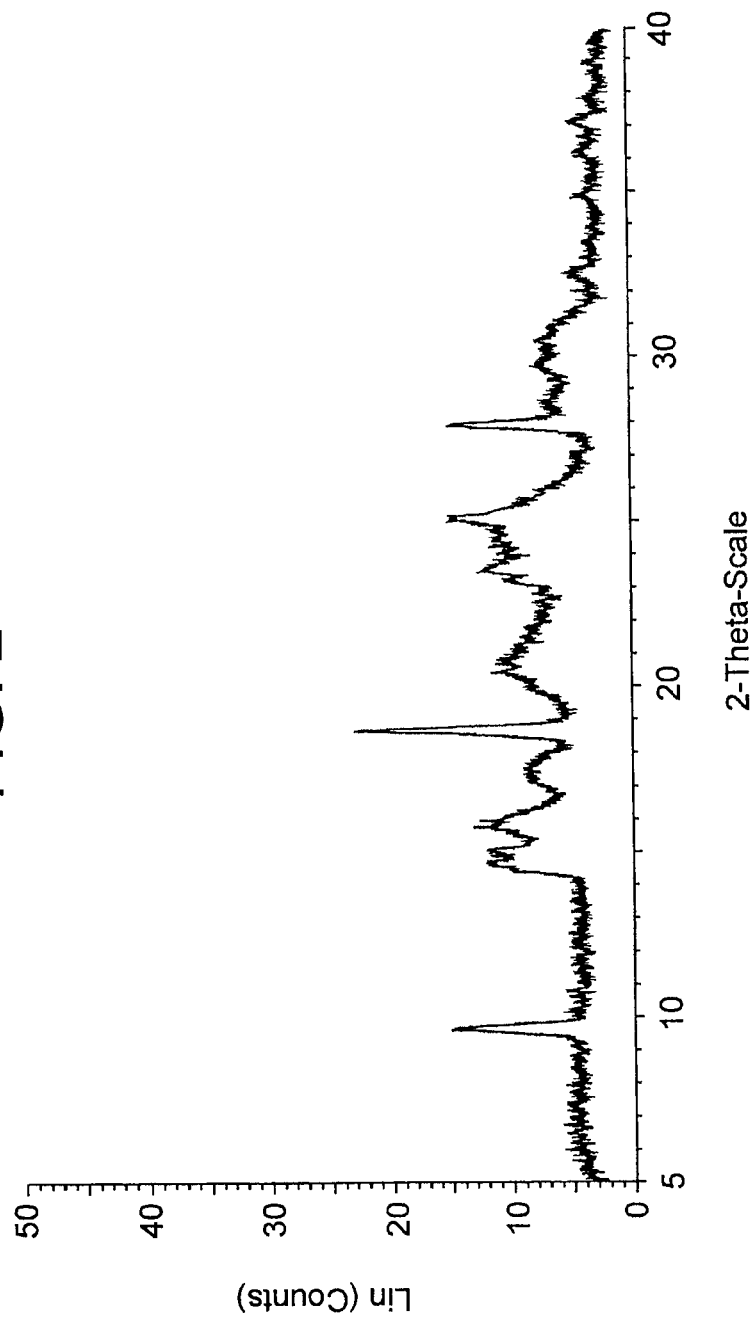
FIG. 2 depicts an X-ray powder diffraction (XRPD) spectrum for Form X.

Form X was found as another solid form in the solubility study. A typical XRPD pattern of form X is shown in FIG. 2.

(2) Crystallization Behavior in 98 v/v % Aqueous Acetonitrile

Form I crystals were added to 98 v/v % aqueous acetonitrile in a glass vessel. Next, 98 v/v % aqueous acetonitrile was added to make the mixture 40 v/w times relative to the Form I crystal. The mixture was stirred with Teflon-coated magnetic stirrer bar and heated to 80° C. with aluminum block. After the crystals were dissolved, the mixture was cooled to a determined temperature at the rate of 30° C. per hour. After a determined holding time, Form I crystals were added as seed crystals according to object of an experiment. Precipitates were sampled periodically and analyzed by XRPD.

Initial precipitates in 98 v/v % aqueous acetonitrile system were confirmed as Form X. Spontaneous transformation from Form X to Form I was not observed within 16 hours. From the results of the seeded experiments, it was estimated that Form I is more stable than Form X regardless of temperature. Form X could be recovered in 84.7% yield.

TABLE 4

Results of crystallization experiments in 98 v/v % aqueous acetonitrile

| Run | Temperature [° C.] | Holding time [hr] | Crystal form |
|---|---|---|---|
| 1 | 60 | 0 | X |
| | 40 | 0 | X |
| | 10 | 0 | X |
| | | 15 | X |
| | | Seeding* | |
| | | 2 | X |
| | | 8 | X |
| | | 27 | X(I)** |
| 2 | 60 | 0 | X |
| | 40 | 0 | X |
| | | 16 | X |
| | | Seeding* | |
| | | 2 | I + X |
| | | 8 | I |
| | | 27 | I |
| 3 | 60 | 0 | X |
| | 40 | 0 | X |
| | 10 | 0 | X |
| | | 15 | X |
| | | — | X |

*ca. 4% w/w Form I crystals
**Slight amount of Form I was detected (3) Transformation Behavior in 98 v/v % Aqueous Acetonitrile Form I crystals and 40 v/w times volume of 98 v/v % aqueous acetonitrile were added to a glass vessel. The mixture was stirred with Teflon-coated magnetic stirrer bar and heated to 80° C. with aluminum block. After dissolved, solution was cooled to 5° C. at the rate of 30° C. per hour. To the slurry of Form X, 10 w/w % of Form I crystals were added as seed crystals at 5° C., then controlled to a certain temperature. Samples of solid material were analyzed by XRPD on a periodic basis.

Transformation from Form X to Form I was observed above ambient temperature. This tendency to transform was also observed at 5° C. In 98 v/v % aqueous acetonitrile system, it was estimated that Form I is more stable than Form X regardless of temperature though transformation kinetics was extremely slow at a low temperature.

TABLE 5

Results of transformation experiments in 98 v/v % aqueous acetonitrile

| Run | Temperature [° C.] | Time [hr] | Crystal form |
|---|---|---|---|
| 1 | 5 | 0* | X |
| | | 16 | X |
| | | 40 | X(I)** |
| 2 | 25 | 0* | X |
| | | 16 | I + X |
| | | 40 | I |
| 3 | 40 | 0* | X |
| | | 16 | I |
| | | 40 | I |

*Right after the seeding at 5° C.
**Slight amount of Form I was detected (4) Transformation behavior in 97 v/v % aqueous acetonitrile Form X crystals and 97 v/v % aqueous acetonitrile were added to a glass vessel. The mixture was stirred with Teflon-coated magnetic stirrer bar at the temperature controlled with aluminum block. Solid component was sampled periodically and analyzed by XRPD to determine the crystal form.

Spontaneous transformation from Form X to Form I was observed in all experiments. It was estimated that Form I is more stable than Form X regardless of temperature in 97 v/v % aqueous acetonitrile.

TABLE 6

Results of transformation experiments in 97 v/v % aqueous acetonitrile

| Run | Temperature [° C.] | Time [hr] | Crystal form |
|---|---|---|---|
| 1 | 10 | 1 | X |
| | | 3 | X |
| | | 21 | I |
| 2 | 20 | 1 | X |
| | | 3 | X |
| | | 21 | I |

TABLE 6-continued

Results of transformation experiments in 97 v/v % aqueous acetonitrile

| Run | Temperature [° C.] | Time [hr] | Crystal form |
|---|---|---|---|
| 3 | 30 | 1 | X |
|   |    | 3 | I |
|   |    | 21 | I |
| 4 | 40 | 1 | X |
|   |    | 3 | I |
|   |    | 21 | I |
| 5 | 50 | 1 | I |
|   |    | 3 | I |
|   |    | 21 | I |

Example 8

Inter-Conversion Tests in Various Solvents

A mixture of crystalline Forms I and II (25 mg/25 mg) was stirred in 0.5 mL of each organic solvent/water shown in Table 7 for 3 days at 5, 25, 40 and 60° C., respectively, and the precipitates were filtrated, then the crystal forms were confirmed by XRPD. The results were shown in the Table 7.

TABLE 7

Results of inter-conversion tests in various solvents

| Solvent | Water Concentration [v/v %] | Temperature[° C.] | | | |
|---|---|---|---|---|---|
|   |   | 5 | 25 | 40 | 60 |
| 2-Propanol | 0 | I(II) | I(II) | I(II) | I |
| 2-Propanol | 2 | I(II) | I | I | X |
| 2-Propanol | 5 | I | I | I | I |
| 2-Propanol | 10 | II | I | I | sol |
| 1-Propanol | 0 | I/X | I/X | I/II | I/II |
| 1-Propanol | 2 | I | X | I | sol |
| 1-Propanol | 5 | I | I | I(II) | sol |
| 1-Propanol | 10 | II | sol | sol | sol |
| Acetone | 0 | I | I/II | I/X | — |
| Acetone | 2 | I | I | I | — |
| Acetone | 5 | I | I | I | — |
| Acetone | 10 | II | I | I | — |
| 1-Butanol | 0 | I | I | I | I |
| 1-Butanol | 2 | I | I | I | I |
| 1-Butanol | 5 | II | I | I | I |
| 1-Butanol | 10 | II | sol | Sol | sol |
| 2-Butanol | 0 | I | I | I | I |
| 2-Butanol | 2 | I | I | I | I |
| 2-Butanol | 5 | II | I | I | I |
| 2-Butanol | 10 | II | II | II | sol |
| Acetonitrile | 0 | I/II | I | I | I |
| Acetonitrile | 2 | I/II | I | I | I |
| Acetonitrile | 5 | II | I | I | I |
| Acetonitrile | 10 | II | II | I/II | sol |
| 2-Butanone | 0 | I | I/X | I/X | I/X |
| 2-Butanone | 2 | II | I | I | I |
| 2-Butanone | 5 | II | II | II | I |
| 2-Butanone | 10 | II | sol | sol | sol |

I: form I
II: form II
I(II): form-I (small amount of form-II)
I/II: form-I/II mixture
I/X: form-I/X mixture
Sol: solution Example 9

Relationship Between Water Concentrations and the Values of Water Activity at Various Temperatures The values of water activity of various water concentrations (i.e., 0, 1, 2, 3, 4, 5, 6, 7, 8, 9, 10 and 20 v/v %) in various organic solvents (i.e., 1-propanol, 2-propanol, 1-butanol, 2-butanol, acetone, 2-butanone, and acetonitrile) at various temperatures (i.e., 0, 5, 10, 15, 20, 25, 30, 35, 40, 45, 50, 55 and 60° C.), respectively, were calculated using COSMOTHERME version 2.1 based on Cosmo-RS method.

Figure 3:
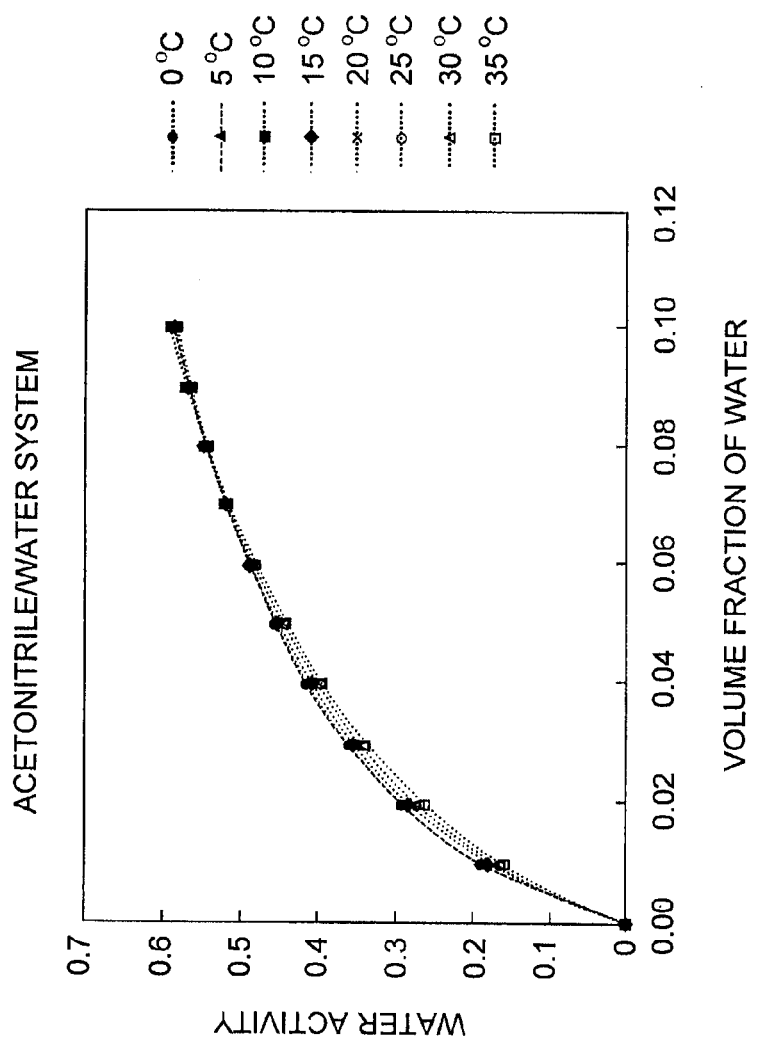
FIG. 3 is a graph depicting the relationship between water activity and volume fraction of water in acetonitrile/water systems at various temperatures.

The values of water concentrations (v/v %) were calculated on the boundary line (equation (6)) between Form I and Form II at various temperatures (i.e., 0, 5, 10, 15, 20, 25, 30, and 35° C.), and converted into the values of water activity using a regression curve of the cubic equation for plots of the values of water activity versus water concentrations at various temperatures (FIG. 3). Table 8 indicates the relationship between water contents (v/v %) and the values of water activity on the boundary line of the phase diagram. The values of water activity and the corresponding temperatures were fitted by equation (7) with a good correlation (correlation coefficient: 0.997).

$$T = 183X - 64.2 \quad (7)$$

TABLE 8

Relationship between water concentrations (v/v %) and the values of water activity at various temperatures

| Temperature [° C.] | Water Concentration [V/V %] | Water activity |
|---|---|---|
| 0 | 2.77 | 0.349 |
| 5 | 3.27 | 0.382 |
| 10 | 3.79 | 0.411 |
| 15 | 4.37 | 0.437 |
| 20 | 5.01 | 0.460 |
| 25 | 5.77 | 0.483 |
| 30 | 6.76 | 0.509 |
| 35 | 8.48 | 0.551 |

The results of the inter-conversion tests were plotted and the boundary line by equation (7) was drawn on the phase diagram of Form I and Form II as shown in FIG. 4. The boundary line approximately separated the Form I and Form II in all experimented solvent systems.

Example 10

Crystallization of Crystalline Form I (1) 1-Propanol

Crystalline Form I (100.1 mg) was dissolved in 1 mL of 1-propanol/water (9:1(v/v)) at 70° C. The mixture was gradually cooled to 60° C. during 20 minutes, and 1 mL of 1-propanol was added thereto. The mixture was again gradually cooled to 5° C. during 110 minutes with stirring. Then 3 mL of 1-propanol was added thereto, and the mixture was stirred at 5° C. overnight. The crystals were isolated by filtration in vacuo and dried under air at room temperature to give crystalline Form I (11.1 mg).

(2) 2-Propanol

Crystalline Form I (100.1 mg) was dissolved in 1 mL of 2-propanol/water (9:1(v/v)) at 90° C. The mixture was gradually cooled to 25° C. during 130 minutes, and 1 mL of 2-propanol was added thereto. The mixture was again gradually cooled to 5° C., and 3 mL of 2-propanol was added. The mixture was stirred at 5° C. for 4 days. The crystals were isolated by filtration in vacuo and dried under air at room temperature to give crystalline Form I (48.9 mg).

(3) 1-Butanol

Crystalline Form I (100.0 mg) was dissolved in 1 mL of 1-butanol/water (9:1(v/v)) at 60° C., and 1 mL of 1-butanol was added thereto. The mixture was gradually cooled to 25° C. during 70 minutes, and 3 mL of 1-butanol was added thereto. The mixture was again gradually cooled to 5° C., and stirred at 5° C. overnight. The crystals were isolated by filtration in vacuo and dried under air at room temperature to give crystalline Form I (29.0 mg).

(4) 2-Butanol

Crystalline Form I (100.0 mg) was dissolved in 1 mL of 2-butanol/water (9:1(v/v)) at 90° C. The mixture was gradually cooled to 60° C. during 60 minutes, and 1 mL of 2-butanol was added thereto. The mixture was gradually cooled to 25° C. during 70 minutes, and 3 mL of 2-butanol was added thereto. The mixture was again gradually cooled to 5° C., and stirred at 5° C. overnight. The crystals were isolated by filtration in vacuo and dried under air at room temperature to give crystalline Form I (52.1 mg).

(5) Acetone

Crystalline Form I (100.2 mg) was dissolved in 1.3 mL of acetone/water (9:1(v/v)) under reflux. The mixture was gradually cooled to 25° C. during 70 minutes, and 1.3 mL of acetone was added thereto. The mixture was gradually cooled to 5° C., and 3.9 mL of acetone was added thereto. The mixture was stirred for 4 days at 5° C. The crystals were isolated by filtration in vacuo and dried under air at room temperature, to give crystalline Form I (74.5 mg).

(6) 2-Butanone

Crystalline Form I (100.3 mg) was dissolved in 1 ml of 2-butanone/water (9:1(v/v)) at 60° C. 4 mL of 2-butanone was added thereto. The mixture was gradually cooled to 25° C. during 70 minutes, and the mixture was stirred at room temperature for 4 days. The crystals were isolated by filtration in vacuo and dried under air at room temperature to give crystalline Form I (70.0 mg).

Example 11

Crystallization of Crystalline Form II (1) 1-Propanol

Crystalline Form I (100.0 mg) was dissolved in 1 mL of 1-propanol/water (9:1(v/v)) at 60° C. The mixture was gradually cooled to 5° C. during 110 minutes, and was stirred for 4 days at 5° C. The crystals were isolated by filtration in vacuo and dried under air at room temperature to give crystalline Form II (11.0 mg).

(2) 2-Propanol

Crystalline Form I (100.3 mg) was dissolved in 1 mL of 2-propanol/water (9:1(v/v)) at 90° C. The mixture was gradually cooled to 5° C. during 170 minutes, and was stirred for 5 days at 5° C. The crystals were isolated by filtration in vacuo and dried under air at room temperature to give crystalline Form II (40.2 mg).

(3) 1-Butanol

Crystalline Form I (100.1 mg) was dissolved in 1 mL of 1-butanol/water (9:1(v/v)) at 70° C. The mixture was gradually cooled to 5° C. during 130 minutes, and 1 mL of 1-butanol was added thereto. The mixture was stirred for 4 days at 5° C. The crystals were isolated by filtration in vacuo and dried under air at room temperature to give crystalline Form II (31.6 mg).

(4) 2-Butanol

Crystalline Form I (100.2 mg) was dissolved in 1 mL of 2-butanol/water (9:1(v/v)) at 90° C. The mixture was gradually cooled to 5° C. during 170 minutes, and 1 mL of 2-butanol was added thereto. The mixture was stirred for 4 days at 5° C. The crystals were isolated by filtration in vacuo and dried under air at room temperature to give crystalline Form II (54.7 mg).

(5) Acetone

Crystalline Form I (100.3 mg) was dissolved in 1.2 mL of acetone/water (9:1(v/v)) under reflux. The mixture was gradually cooled to 5° C. 110 minutes, and 1 mL of acetone was added thereto. The mixture was stirred for 4 days at 5° C. The crystals were isolated by filtration in vacuo and dried under air at room temperature to give crystalline Form II (36.4 mg).

(6) 2-Butanone

Crystalline Form I (100.2 mg) was dissolved in 1 mL of 2-butanone/water (9:1(v/v)) at 60° C. The mixture was cooled to 5° C. during 110 minutes. Next, 4 mL of 2-butanone was added thereto. The mixture was stirred for 4 days at 5° C. The crystals were isolated by filtration in vacuo and dried under air at room temperature to give crystalline Form II (76.7 mg).

Example 12

Physical Data of Forms I and II (1) Powder X-Ray Diffraction (XRD)

Diffraction patterns were taken at room temperature and humidity using a Rigaku RINT-TTRIII diffractometer with Cu Kα radiation. The diffraction angle, 2θ, was scanned from 3 to 40 at rate of 2°/minute at a step size of 0.02°. The results of this analysis are shown in FIGS. 5 and 6, which are the same as those measured against an internal silicon standard.

(2) Solubility

Excess amount of the samples, Forms I and II, were suspended in water, and were equilibrated by shaking for 20 minutes at 25° C. or 37° C., respectively. The amounts of dissolved the compound were determined using a Waters alliance HPLC system 2695, detected by UV 210 nm. The results of this analysis are shown in Table 9.

TABLE 9

Solubility in water of the crystalline Forms I and II

| Temperature | Form I | Form II |
|---|---|---|
| 25° C. | 39 mg/mL | 30 mg/mL |
| 37° C. | 90 mg/mL | 54 mg/mL |

(3) Hygroscopicity

The hygroscopicity of Forms I and II were investigated using a Surface measurement systems, DVS-1, between 10% RH and 90% RH at 25° C. There was no hygroscopicity in Form I. On the other hand, there was a hygroscopicity in Form II, and the water value of approximately 4% was increased and decreased between 10% RH and 90% RH by absorption and desorption of ca. 1 mol of channel water.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

The invention claimed is:

1. A method of improving cognition in a patient suffering from Schizophrenia, comprising administering to the patient a crystalline Form I of (R)-7-chloro-N-(quinuclidin-3-yl)benzo[b]thiophene-2-carboxamide hydrochloride monohydrate.

2. The method of claim 1, wherein the crystalline Form I of (R)-7-chloro-N-(quinuclidin-3-yl)benzo[b]thiophene-2-carboxamide hydrochloride monohydrate is characterized by an x-ray powder diffraction pattern having peaks expressed as 2Θ at:
   i) one or both of 17.48 and 20.58±0.20 degrees when measured against an internal silicon standard; and
   ii) at least four peaks selected from a group of peaks consisting of: 4.50, 9.04, 14.60, 15.14, 15.80, 16.60, 18.16, 18.44, 19.48, 21.74 and 25.46±0.20 degrees when measured against an internal silicon standard.

3. The method of claim 2, wherein the crystalline Form I is characterized by an x-ray powder diffraction pattern with at least six peaks selected from the group of peaks.

4. The method of claim 2, wherein the crystalline Form I is characterized by an x-ray powder diffraction pattern with at least eight peaks selected from the group of peaks.

5. The method of claim 2, wherein the crystalline Form I is characterized by an x-ray powder diffraction pattern with all of the peaks selected from the group of peaks.

6. The method of claim 1, wherein the method further treats cognitive loss in the patient.

7. The method of claim 6, wherein the patient is over age 60.

8. The method of claim 6, wherein the patient further suffers from age-related memory loss.

9. A method of improving cognition in a patient suffering from Alzheimer's Disease, comprising administering to the patient a pharmaceutical composition comprising a crystalline Form I of (R)-7-chloro-N-(quinuclidin-3-yl)benzo[b]thiophene-2-carboxamide hydrochloride monohydrate.

10. The method of claim 9, wherein the crystalline Form I of (R)-7-chloro-N-(quinuclidin-3-yl)benzo[b]thiophene-2-carboxamide hydrochloride monohydrate is characterized by an x-ray powder diffraction pattern having peaks expressed as 2Θ at:
    i) one or both of 17.48 and 20.58±0.20 degrees when measured against an internal silicon standard; and
    ii) at least four peaks selected from a group of peaks consisting of: 4.50, 9.04, 14.60, 15.14, 15.80, 16.60, 18.16, 18.44, 19.48, 21.74 and 25.46±0.20 degrees when measured against an internal silicon standard.

11. The method of claim 10, wherein the crystalline Form I is characterized by an x-ray powder diffraction pattern with at least six peaks selected from the group of peaks.

12. The method of claim 10, wherein the crystalline Form I is characterized by an x-ray powder diffraction pattern with at least eight peaks selected from the group of peaks.

13. The method of claim 10, wherein the crystalline Form I is characterized by an x-ray powder diffraction pattern with all of the peaks selected from the group of peaks.

14. The method of claim 9, wherein the method further treats cognitive loss in the patient.

15. The method of claim 14, wherein the patient is over age 60.

16. The method of claim 14, wherein the patient further suffers from age-related memory loss.

* * * * *